United States Patent [19]

Lynch et al.

[11] Patent Number: 5,710,129
[45] Date of Patent: Jan. 20, 1998

[54] INHIBITORS OF SH2-MEDIATED PROCESSES

[75] Inventors: Berkley A. Lynch; Manfred Weigele, both of Cambridge, Mass.

[73] Assignee: Ariad Pharmaceuticals, Inc., Cambridge, Mass.

[21] Appl. No.: 392,646

[22] Filed: Feb. 23, 1995

[51] Int. Cl.[6] .................... A61K 38/04; C07K 5/10
[52] U.S. Cl. .................... 514/18; 530/330; 560/21; 560/29
[58] Field of Search .................... 560/29, 21; 514/18; 530/330

[56] References Cited

PUBLICATIONS

Jankauskas, et al., Fiziol.Akt. Vsehchestva (1988), 20,11–16 [abstract supplied—CA110:18505].
Stewart, et al., Aust. J. Chem. (1979), 32 (3),661–7 [abstract supplied—CA91:91946].

Primary Examiner—Robert Gerstl
Attorney, Agent, or Firm—David L. Berstein

[57] ABSTRACT

This invention relates to compounds of formula:

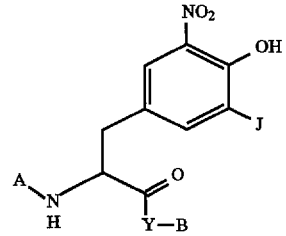

and pharmaceutically acceptable salts thereof, where A is H, $R^1$, —CO—$R^1$ or —CO—$OR^1$ where $R^1$ is a substituted or unsubstituted alkyl, heteroalkyl, aryl or heteroaryl group and J is H or $NO_2$. L-forms of the compounds are currently preferred, although D-forms and racemic mixtures are also encompassed by this invention.

8 Claims, No Drawings

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note=
         " N-(Fmoc)-3,5-dinitro-L-tyrosine"

( i x ) FEATURE:
      ( A ) NAME/KEY: Modified-site
      ( B ) LOCATION: 4
      ( D ) OTHER INFORMATION: /product="amidated"

( x i ) SEQUENCE DESCRIPTION: SEQ ID NO:1:

Tyr  Glu  Thr  Leu
   1

( 2 ) INFORMATION FOR SEQ ID NO:2:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note=
         " N-(Fmoc)-3,5-dinitro-L-tyrosine"

( i x ) FEATURE:
      ( A ) NAME/KEY: Modified-site
      ( B ) LOCATION: 4
      ( D ) OTHER INFORMATION: /product="amidated"

( x i ) SEQUENCE DESCRIPTION: SEQ ID NO:2:

Tyr  Asp  Val  Leu
   1

( 2 ) INFORMATION FOR SEQ ID NO:3:

( i ) SEQUENCE CHARACTERISTICS:
  ( A ) LENGTH: 4 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note=
      " N-(Fmoc)-3,5-dinitro-L-tyrosine"

( i x ) FEATURE:
  ( A ) NAME/KEY: Modified-site
  ( B ) LOCATION: 4
  ( D ) OTHER INFORMATION: /product="amidated"

( x i ) SEQUENCE DESCRIPTION: SEQ ID NO:3:

Tyr Thr Gly Leu
1

( 2 ) INFORMATION FOR SEQ ID NO:4:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note=
        " N-(Fmoc)-3,5-dinitro-L-tyrosine"

( i x ) FEATURE:
    ( A ) NAME/KEY: Modified-site
    ( B ) LOCATION: 4
    ( D ) OTHER INFORMATION: /product="amidated"

( x i ) SEQUENCE DESCRIPTION: SEQ ID NO:4:

Tyr Asn Glu Leu
1

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note=
        " N-(Fmoc)-3,5-dinitro-L-tyrosine"

( i x ) FEATURE:
    ( A ) NAME/KEY: Modified-site
    ( B ) LOCATION: 4
    ( D ) OTHER INFORMATION: /product="amidated"

( x i ) SEQUENCE DESCRIPTION: SEQ ID NO:5:

Tyr Glu Thr Leu
1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " N-(3-phenylproprionyl)-3,5-dinitro-L-tyrosine"

( i x ) FEATURE:
        ( A ) NAME/KEY: Modified-site
        ( B ) LOCATION: 4
        ( D ) OTHER INFORMATION: /product="amidated"

( x i ) SEQUENCE DESCRIPTION: SEQ ID NO:6:

Tyr  Glu  Thr  Leu
  1

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " N-(3,3-diphenylproprionyl)-3,5-dinitro-L-tyrosine"

( i x ) FEATURE:
        ( A ) NAME/KEY: Modified-site
        ( B ) LOCATION: 4
        ( D ) OTHER INFORMATION: /product="amidated"

( x i ) SEQUENCE DESCRIPTION: SEQ ID NO:7:

Tyr  Glu  Thr  Leu
  1

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " N-(1-naphthylacetyl)-3,5-dinitro-L-tyrosine"

( i x ) FEATURE:
        ( A ) NAME/KEY: Modified-site
        ( B ) LOCATION: 4
        ( D ) OTHER INFORMATION: /product="amidated"

( x i ) SEQUENCE DESCRIPTION: SEQ ID NO:8:

Tyr  Glu  Thr  Leu
  1

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " N-(2-naphthoyl)-3,5-dinitro-L-tyrosine"

( i x ) FEATURE:
        ( A ) NAME/KEY: Modified-site
        ( B ) LOCATION: 4
        ( D ) OTHER INFORMATION: /product="amidated"

( x i ) SEQUENCE DESCRIPTION: SEQ ID NO:9:

Tyr  Glu  Thr  Leu
    1

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " N-(2-naphthylacetyl)-3,5-dinitro-L-tyrosine"

( i x ) FEATURE:
        ( A ) NAME/KEY: Modified-site
        ( B ) LOCATION: 4
        ( D ) OTHER INFORMATION: /product="amidated"

( x i ) SEQUENCE DESCRIPTION: SEQ ID NO:10:

Tyr  Glu  Thr  Leu
    1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " N-(3-methyl-3-phenylproprionyl)-3,5-dinitro-L-tyrosine"

( i x ) FEATURE:
        ( A ) NAME/KEY: Modified-site
        ( B ) LOCATION: 4
        ( D ) OTHER INFORMATION: /product="amidated"

( x i ) SEQUENCE DESCRIPTION: SEQ ID NO:11:

Tyr  Glu  Thr  Leu
    1

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "N-acetylated"

( i x ) FEATURE:
        ( A ) NAME/KEY: Modified-site
        ( B ) LOCATION: 2
        ( D ) OTHER INFORMATION: /note= "3,5-dinitro-L-tyrosine"

( i x ) FEATURE:
        ( A ) NAME/KEY: Modified-site
        ( B ) LOCATION: 5
        ( D ) OTHER INFORMATION: /product="amidated"

( x i ) SEQUENCE DESCRIPTION: SEQ ID NO:12:

```
Phe  Tyr  Glu  Thr  Leu
1                    5
```

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "N-acetyl-D-phenylalanine"

( i x ) FEATURE:
        ( A ) NAME/KEY: Modified-site
        ( B ) LOCATION: 2
        ( D ) OTHER INFORMATION: /note= "3,5-dinitro-L-tyrosine"

( i x ) FEATURE:
        ( A ) NAME/KEY: Modified-site
        ( B ) LOCATION: 5
        ( D ) OTHER INFORMATION: /product="amidated"

( x i ) SEQUENCE DESCRIPTION: SEQ ID NO:13:

```
Phe  Tyr  Glu  Thr  Leu
1                    5
```

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "N-acetyl-2-naphthylalanine"

( i x ) FEATURE:

(A) NAME/KEY: Modified-site
(B) LOCATION: 5
(D) OTHER INFORMATION: /product="amidated"

(xi) SEQUENCE DESCRIPTION: SEQ ID NO:14:

Xaa Tyr Glu Thr Leu
1               5

(2) INFORMATION FOR SEQ ID NO:15:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "N-acetyl-1-naphthylalanine"

(ix) FEATURE:
    (A) NAME/KEY: Modified-site
    (B) LOCATION: 5
    (D) OTHER INFORMATION: /product="amidated"

(xi) SEQUENCE DESCRIPTION: SEQ ID NO:15:

Xaa Tyr Glu Thr Leu
1               5

(2) INFORMATION FOR SEQ ID NO:16:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "N-Fmoc-3-nitro-L-tyrosine"

(ix) FEATURE:
    (A) NAME/KEY: Modified-site
    (B) LOCATION: 4
    (D) OTHER INFORMATION: /product="amidated"

(xi) SEQUENCE DESCRIPTION: SEQ ID NO:16:

Tyr Glu Thr Leu
1

(2) INFORMATION FOR SEQ ID NO:17:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note=
        " N-acetyl-3-nitro-L-tyrosine"

(ix) FEATURE:
    (A) NAME/KEY: Modified-site (B) LOCATION: 5
                (D) OTHER INFORMATION: /product="amidated"

(xi) SEQUENCE DESCRIPTION: SEQ ID NO:17:

Tyr  Glu  Glu  Ile  Pro
    1                    5

(2) INFORMATION FOR SEQ ID NO:18:

(i) SEQUENCE CHARACTERISTICS:
                (A) LENGTH: 19 amino acids
                (B) TYPE: amino acid
                (C) STRANDEDNESS: single
                (D) TOPOLOGY: linear (ii) MOLECULE TYPE: protein (v) FRAGMENT TYPE: internal (ix) FEATURE:
                (A) NAME/KEY: Modified-site
                (B) LOCATION: 4
                (D) OTHER INFORMATION: /product="phosphotyrosine"
                        / label= YPO4
                        / note= "phosphorylated tyrosine"

(ix) FEATURE:
                (A) NAME/KEY: Modified-site
                (B) LOCATION: 15
                (D) OTHER INFORMATION: /product="phosphotyrosine"
                        / label= YPO4
                        / note= "phosphorylated tyrosine"

(xi) SEQUENCE DESCRIPTION: SEQ ID NO:18:

Asp  Gly  Val  Tyr  Thr  Gly  Leu  Ser  Thr  Arg  Asn  Gln  Glu  Thr  Tyr  Glu
    1                   5                            10                          15

Thr  Leu  Lys (2) INFORMATION FOR SEQ ID NO:19:

(i) SEQUENCE CHARACTERISTICS:
                (A) LENGTH: 22 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 7
                (D) OTHER INFORMATION: /product="phosphotyrosine"
                        / label= YPO4
                        / note= "phosphorylated tyrosine"

(ix) FEATURE:
                (A) NAME/KEY: Modified-site
                (B) LOCATION: 18
                (D) OTHER INFORMATION: /product="phosphotyrosine"
                        / label= YPO4
                        / note= "phosphorylated tyrosine"

(ix) FEATURE:
                (A) NAME/KEY: Modified-site
                (B) LOCATION: 1
                (D) OTHER INFORMATION: /product="Acetylated"
                        / label= Ac (ix) FEATURE:
                (A) NAME/KEY: Modified-site
                (B) LOCATION: 22
                (D) OTHER INFORMATION: /product="Amidated"
                        / label= NH2

(xi) SEQUENCE DESCRIPTION: SEQ ID NO:19:

```
Cys Gly Gly Asp Gly Val Tyr Thr Gly Leu Ser Thr Arg Asn Gln Glu
1               5                   10                  15

Thr Tyr Glu Thr Leu Lys
            20
```

( 2 ) INFORMATION FOR SEQ ID NO:20:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( i x ) FEATURE:
        ( A ) NAME/KEY: Modified-site
        ( B ) LOCATION: 4
        ( D ) OTHER INFORMATION: /product="phosphotyrosine"
            / label= YPO4
            / note= "phosphorylated tyrosine"

( i x ) FEATURE:
        ( A ) NAME/KEY: Modified-site
        ( B ) LOCATION: 15
        ( D ) OTHER INFORMATION: /product="phosphotyrosine"
            / label= YPO4
            / note= "phosphorylated tyrosine"

( x i ) SEQUENCE DESCRIPTION: SEQ ID NO:20:

```
Asn Gln Leu Tyr Asn Glu Leu Asn Ile Gly Arg Arg Glu Glu Tyr Asp
1               5                   10                  15

Val Leu Asp
```

( 2 ) INFORMATION FOR SEQ ID NO:21:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 18
        ( D ) OTHER INFORMATION: /product="phosphotyrosine"
            / label= YPO4
            / note= "phosphorylated tyrosine"

( i x ) FEATURE:
        ( A ) NAME/KEY: Modified-site
        ( B ) LOCATION: 1
        ( D ) OTHER INFORMATION: /product="Acetylated"
            / label= Ac ( i x ) FEATURE:
        ( A ) NAME/KEY: Modified-site
        ( B ) LOCATION: 22
        ( D ) OTHER INFORMATION: /product="Amidated"
            / label= NH2

( i x ) FEATURE:
        ( A ) NAME/KEY: Modified-site
        ( B ) LOCATION: 7
        ( D ) OTHER INFORMATION: /product="phosphotyrosine"
            / label= YPO4
            / note= "phosphorylated tyrosine"

( x i ) SEQUENCE DESCRIPTION: SEQ ID NO:21:

```
Lys Gly Gly Asn Gln Leu Tyr Asn Glu Leu Asn Ile Gly Arg Arg Glu
1               5                   10                  15

Glu Tyr Asp Val Leu Asp
            20
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product="phosphorylated"
            / label= YPO4
            / note= "phosphorylated tyrosine"

(xi) SEQUENCE DESCRIPTION: SEQ ID NO:22:

```
Gln Tyr Glu Glu Ile Pro Ile
1               5
```

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product="N-acetylated"
            / label= Ac (ix) FEATURE:
        (A) NAME/KEY: Modified-site
        (B) LOCATION: 5
        (D) OTHER INFORMATION: /product="phosphotyrosine"
            / label= YPO4
            / note= "phosphorylated tyrosine"

(ix) FEATURE:
        (A) NAME/KEY: Modified-site
        (B) LOCATION: 10
        (D) OTHER INFORMATION: /product="amidated"
            / label= NH2

(xi) SEQUENCE DESCRIPTION: SEQ ID NO:23:

```
Lys Gly Gly Gln Tyr Glu Glu Ile Pro Ile
1               5                   10
```

INHIBITORS OF SH2-MEDIATED PROCESSES

BACKGROUND

One aspect of cellular function in both normal and disease states which has attracted increasing attention is cellular signal transduction, the series of events leading from extracellular events to intracellular sequelae. Numerous proteins that function as signal transducing molecules have been identified. These include receptor and non-receptor tyrosine kinases, phosphatases and other molecules with enzymatic or regulatory activities. A common feature of many of these molecules is their capacity to associate specifically with other proteins to form a signaling complex that can alter cell activity.

Signaling proteins often contain one or more domains of conserved sequence which serve as non-catalytic modules that direct protein-protein interactions during signal transduction. One such domain has been termed the src homology domain 2 (SH2) domain. SH2 domains are relatively small (~100 amino acids for SH2) and are found in various combinations and locations in different proteins. Many proteins which contain one or more SH2 domains are already known, including the fps/fes family of protein tyrosine kinases (PTKs), ISGF3alpha p113, p91/84, Tensin, shc; syk, zap, PTPase 1C and PTPase 2; src and the src family of PTKs, abl and the abl family of PTKs, csk, tec; PLCgamma 1 and 2, GAP, p85alpha and p85 beta; vav, c-crk and GRB2; and nck.

Aspects of the structures of some SH2 domains are known and certain aspects of their role in signal transduction is becoming better understood. SH2 domains direct the association of specific proteins by binding selectively and with specificity to protein sequences containing phosphotyrosine. For example, upon binding of PDGF to the PDGF β-receptor, the receptor dimerizes and autophosphorylates multiple tyrosine residues. This phosphorylation triggers the physical association of SH2-containing proteins such as c-src, PLC-gamma, PI3K and ras-GAP with the receptor, forming a signaling complex. An analysis of SH2 binding using natural ligands containing mutations at residues surrounding the site of phosphorylation as well as a screen of combinatorial peptide libraries using SH2 domains has provided data on phosphopeptide sequence specificity of SH2 binding.

Pharmaceutical agents which interfere with the formation or stability of signaling complexes formed by proteins containing one or more SH2 domains and their natural ligands could be used to treat or prevent the diseases or their pathological effects mediated by such complexes. Unfortunately, while phosphotyrosine has been considered a required component of an SH2 binding compound, in view of pharmacokinetic and drug delivery issues, agents other than phosphorylated tyrosine-containing oligopeptides would be particularly desirable.

SUMMARY OF THE INVENTION

This invention relates to compounds of formula:

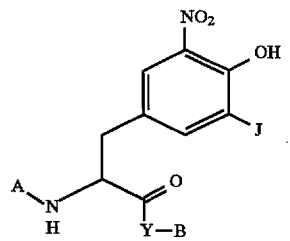

and pharmaceutically acceptable salts thereof, where A is H, $R^1$, —CO—$R^1$ or —CO—$OR^1$ where $R^1$ is a substituted or unsubstituted alkyl, heteroalkyl, aryl or heteroaryl group and J is H or $NO_2$. L-forms of the compounds are currently preferred, although D-forms and racemic mixtures are also encompassed by this invention, as are N-alkylated derivatives thereof.

Alkyl, as the term is used herein, is intended to include saturated and unsaturated, linear (straight-chain), branched, cyclic, and polycyclic aliphatic hydrocarbons, generally containing 1–10 contiguous aliphatic carbon atoms, which are optionally substituted with one or more functional groups selected from the group consisting of hydroxy, $C_1$–$C_8$ alkoxy, acyloxy, carbamoyl, amino, N-acylamino, keto, halo (chloro, bromo, fluoro or iodo), trihalomethyl, cyano, carboxyl, alkyl, cycloalkyl, aryl and heteroaryl, which functional groups may themselves (with the exception of hydroxy, halo and cyano groups) bear one or more of the foregoing functional groups. Preferably alkyl, alkoxy and acyl groups contain 1–6 contiguous aliphatic carbon atoms, and may bear substituents.

Aryl, as the term is used herein, is intended to include stable cyclic, heterocyclic, polycyclic, and polyheterocyclic unsaturated $C_3$–$C_{14}$ moieties (exemplified by but not limited to phenyl, biphenyl, naphthyl, pyridyl, furyl, thiophenyl, imidazoyl, pyrimidinyl, and oxazoyl) which may be substituted with one to five functional groups selected from the group consisting of hydroxy, $C_1$–$C_8$ alkoxy, $C_1$–$C_8$ branched or straight-chain alkyl, acyloxy, carbamoyl, amino, N-acylamino, nitro, halo, trifluoromethyl, cyano, and carboxyl, which functional groups may themselves (with the exception of hydroxy, halo, triflouromethyl and cyano groups) bear one or more of the foregoing functional groups.

Heteroalkyl and heteroaryl, as those terms are used herein, refer to alkyl and aryl moieties respectively, which contain one or more of oxygen, sulfur, or nitrogen in place of one or more carbon atoms.

The following illustrative —CO—$R^1$ and —CO—$OR^1$ groups exemplify aryl, arylalkyl and arylcycloalkyl $R^1$ groups:

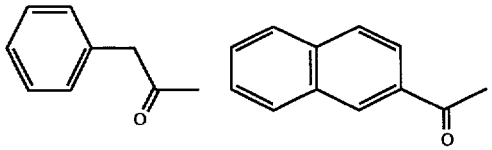

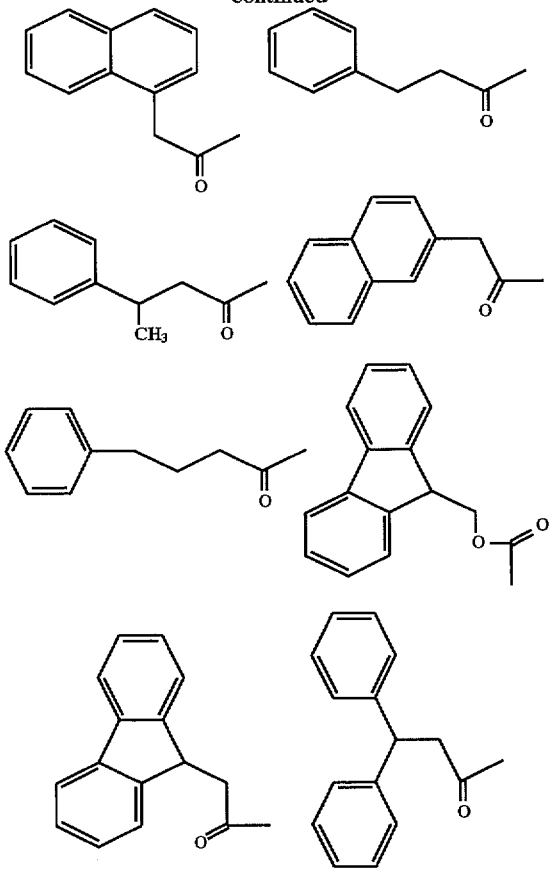

—CO—R¹ may also comprise a substituted or unsubstituted amino acid, itself containing an optional substituent A as previously defined (acetyl in the illustrations below) on its amino group, and an alkyl, aryl, arylalkyl, heteroaryl or heteroarylalkyl substituent on the alpha carbon, including for example:

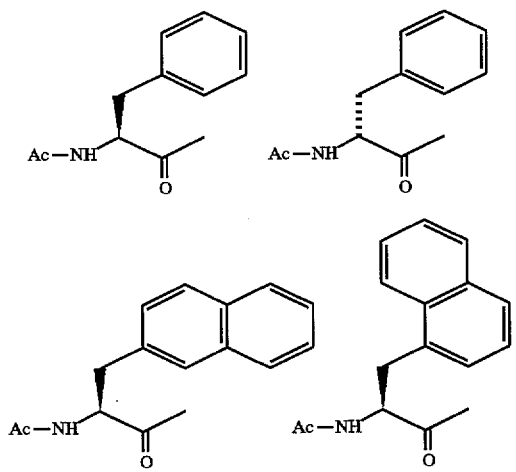

Y is —CH₂—, —O—, or —NH— (which may bear an aryl or alkyl substituent). B is an aryl moiety or an alkyl moiety which may be linear, branched or cyclic (e.g. monocyclic, bicyclic or tricyclic), and in either case, may be further substituted. In some cases B preferably contains a hydrophobic substituent. By "hydrophobic" we mean a moiety comprising at least 3 contiguous carbon atoms. For example, Y-B may be an amino acid (including, among others, hydrophobic amino acids such as Ile, Leu, Nle, Phe, Nal), a dipeptide (such as Glu-Thr, Asp-Val, Glu-Glu, Ser-Glu, or Asn-Glu), a tripeptide, a tetrapeptide or an oligopeptide, comprising one or more D- or L-amino acids (one or more of which may bear alkyl substituents on their alpha nitrogen atom(s)); or an alkyl or aryl ester, amide or carbamate derivative of any of the foregoing. Preferably B is a moiety containing about 6 to 50 atoms, with the proviso that in embodiments in which J is NO₂, where A is tBOC or triflouroacetyl, YB is not -OEt; where A is acetyl, YB is not -OEt, -OMe, or L-Phe; and where A is H, L-phenylalanyl- or N-cbz-L-phenylalanyl-, YB is not -OMe.

Illustrative Y-B substituents containing a monocyclic B moiety include the following:

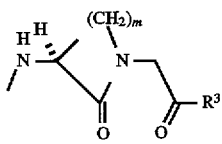

where m is 1, 2 or 3 and $R^3$ is —OH, alkyl, alkoxyl, amino or alkyl or aryl substituted amino, including, e.g., an amino acid, dipeptide or oligopeptide, or an ester, amide or carbamate thereof;

Illustrative Y-B substituents containing a bicyclic B moiety include the following:

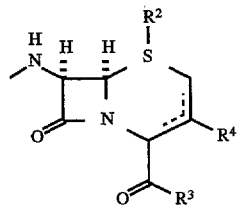

where $R^2$ is —, O or $O_2$; $R^3$ is as defined above; and $R^4$ is H, alkyl or aryl, preferably lower (i.e., 1–6 carbons) alkyl; and

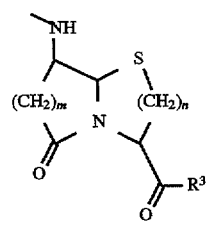

where R3 is as defined above and n and m are independently 1 or 2 (including individual stereoisomers thereof as well as mixtures of one or more of the stereoisomers).

This invention thus includes, among others, compounds of the following formulas, as well as those exemplified elsewhere herein:

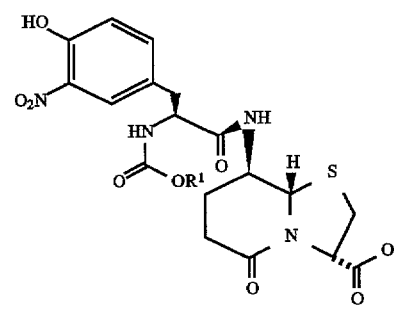
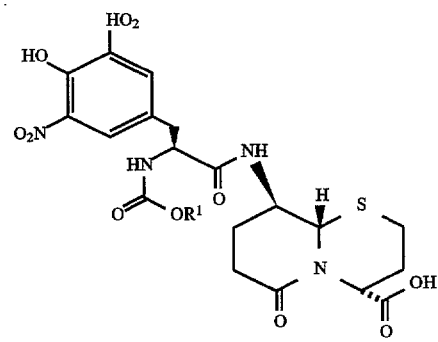
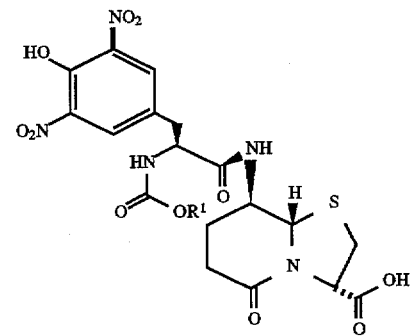
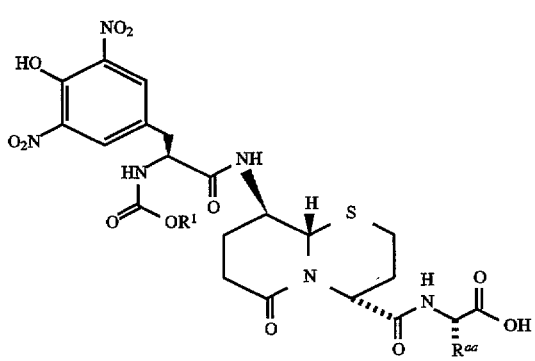
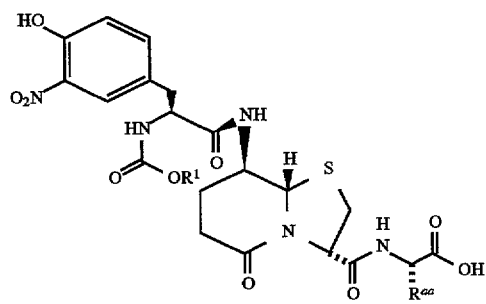
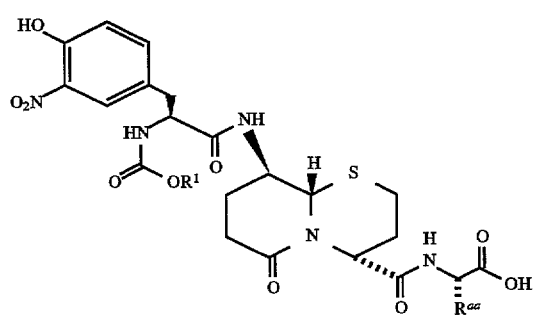
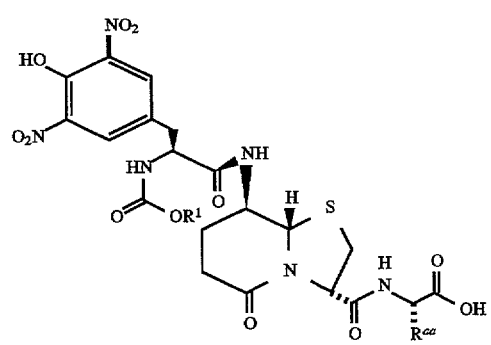
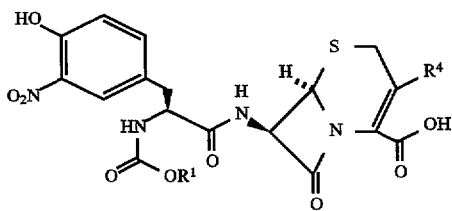
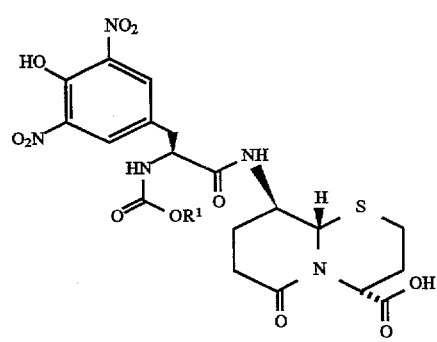
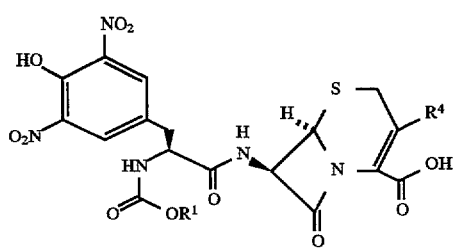

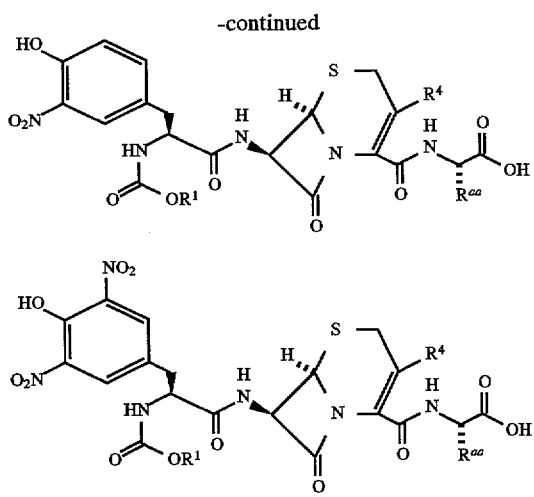

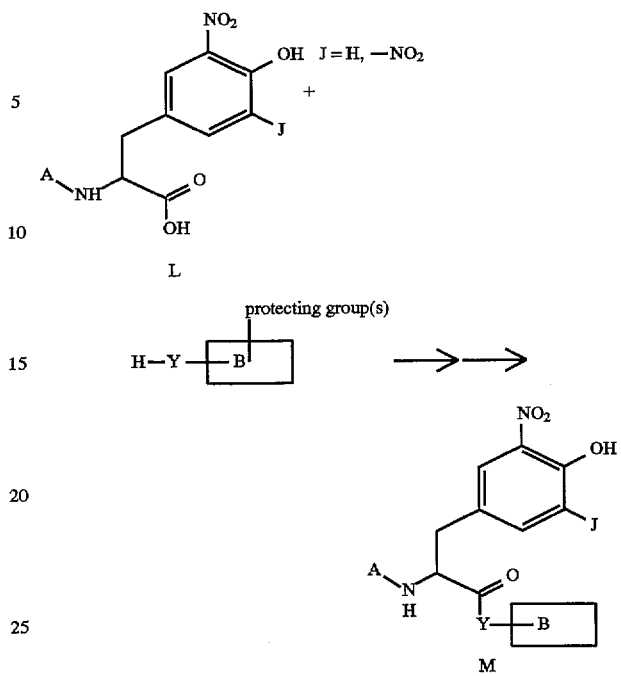

where $R^1$ is an aryl, arylalkyl or arylcycloalkyl group such as are illustrated above; $R^4$ is an alkyl or aryl group and is preferably a C1–6 aliphatic group such as methyl, ethyl, n-propyl, i-propyl, allyl and so forth; $R^{aa}$ is H or an aryl or alkyl group and is preferably a side-chain of a naturally occurring amino acid (e.g., H (glycine), —$CH_3$ (alanine), —$CH_2C_6H_5$ (phenylalanine), and so forth); as well as esters, amides, carbamates and pharmaceutically acceptable salts thereof.

Especially preferred are compounds of this invention which bind to a protein containing at least one SH2 domain with an affinity (i.e. an IC50 value, e.g. an IC50 BIAcore value) of at least about 200 µM, and more preferably at least about 100 µM, and more preferably at least about 50 µM as measured by any assay commonly used in the art. Compounds with IC50 values below 10 µM are of particular interest. Compounds are also preferred which bind to one SH2 domain with an affinity at least an order of magnitude greater than with respect to a different SH2 domain, again, as may be determined by any conventional assay. Compounds of this invention interfere with intermolecular and/or intramolecular interactions which would otherwise be mediated by that SH2 domain. Such compounds are therefore useful as reagents for biological research since, for example, they can be used to uncouple or block a particular signal transduction pathway of interest. Compounds of this invention which interfere with the formation or stability of signaling complexes formed by proteins containing one or more SH2 domains and their natural ligands could be used to treat or prevent the diseases or their pathological effects mediated by such complexes.

Thus, this invention further comprises a method for enhancing the binding of a compound of interest to an SH2 domain, where the compound which contains a YB moiety, which method comprises covalently attaching a moiety of formula L (see below) to the compound of interest to produce a compound of formula M.

Synthesis

In many cases, compounds of this invention may be prepared by condensing a tyrosine derivative, L, (or an activated form thereof) with the desired H-YB compound using conventional materials and methods such as are used routinely in peptide chemistry.

3-Nitro- and 3,5-dinitro derivatives of the formula L (as well as salts thereof and activated forms, such as esters, acid halides and the like) are thus important intermediates, especially where A (in the structure depicted above) is other than H, acetyl, or N-acetyl-L-phenylalanyl in compounds in which J is nitro. 3,5-Dinitrotyrosine intermediates are of particular interest, especially those that contain at least one phenyl substituent such as in the case of N-Fmoc-3,5-dinitro-L-tyrosine. 3-Nitrotyrosine and 3,5-dinitrotyrosine (or N-protected forms thereof, such as the N-Fmoc-derivatives) may be prepared as described herein. The underivatized L-amino acids and N-Fmoc-3-nitro-L-tyrosine may be obtained from commercial sources. They may be modified by the addition of —$R^1$, —$COR^1$ or —$CO(OR^1)$ using conventional methods and materials. Preparation of representative compounds of this invention and intermediates useful for preparing them are detailed in the Experimental Examples which follow.

Functional Characterization of the Compounds

Compounds of this invention may be evaluated for binding activity with respect to one or more SH2 domains of interest, or with respect to proteins containing the SH2 domain(s), using various approaches, a number of which are well known in the art. For instance, compounds may be evaluated for activity as competitive inhibitors of the binding of an SH2 domain with a phosphorylated ligand thereto. See e.g. Pawson, U.S. Pat. No. 5,352,660 (4 Oct. 1994). Compounds may be evaluated for binding to one or more SH2 domains of interest using surface plasmon resonance (BIAcore®) technology. See e.g., Panayotou et al, 1993, Molecular and Cellular Biology 13: 3567–3576.

Compounds may further be evaluated for activity in inhibiting cellular or other biological events mediated by a pathway involving the SH2-based interaction of interest using a suitable cell-based assay or an animal model. Cell-based assays and animal models suitable for evaluating inhibitory actvity of a compound with respect to a wide variety of cellular and other biological events are known in the art. New assays and models are regularly developed and reported in the scientific literature.

By way of non-limiting example, compounds which bind to an SH2 domain involved in the transduction of a signal leading to asthma or allergic episodes may be evaluated in a mast cell or basophil degranulation assay. The inhibitory activity of a compound of this invention with respect to cellular release of specific mediators such as histamine, leukotrienes, hormonal mediators and/or cytokines as well as its biological activity with respect to the levels of phosphatidylinositol hydrolysis or tyrosine phosphorylation can be characterized with conventional in vitro assays as an indication of biological activity. (See e.g."IgE-induced histamine release from rat basophilic leukemia cell lines: isolation of releasing and nonreleasing clones". Edward L. Barsumian, Chaviva Isersky, Marianne G. Petrino and Reuben P. Siraganian. Eur. J. Immunol. 1981. 11:317–323; Forrest, M. J., 1991, Biochemical Pharmacology 42:1221–1228 (measuring N-acetyl-betaglucosaminadase from activated netrophils); and Stephan, V. M., et al., *J. Biol. Chem.* 267:5434–5441 (1992)). For example, histamine release can be measured by a radioimmunoassay using a kit available from AMAC Inc. (Westbrook, Me.). One can thus evaluate the biological activity of compounds of this invention and compare them to one another and to known active compounds such as leflunomide (and its active metabolite, A771726), vanadate, staurosporine, genistein, or clinically relevant compounds which can be used as positive controls. Generally speaking, in such assays $IC_{50}$ scores of 150–300 μM are considered of interest, scores of 50–150 μM are considered good, and scores below about 50 μM are of high interest.

Prior to in vivo models, compounds may also be tested in an ex-vivo assay for their ability to block antigen-stimulated contraction of sensitized guinea pig tracheal strip tissue. Activity in this assay has been shown to be useful in predicting the efficacy of potential anti-asthma drugs. Numerous animal models of asthma have been developed and can be used (for reviews, see Larson, "Experimental Models of Reversible Airway Obstruction", in THE LUNG, Scientific Foundations, Crystal, West et al. (eds.), Raven Press, New York, pp. 953–965 (1991); Warner et al., 1990, *Am. Rev. Respir. Dis.* 141:253–257). Species used in animal models of asthma include mice, rats, guinea pigs, rabbits, dogs, sheep and primates. Other in vivo models available are described in Cross et al., *Lab Invest.* 63:162–170 (1990)); and Koh, et al., *Science*, 256:1210–1213 (1992)).

By way of further example, compounds of this invention which bind to an SH2 domain involved in the transduction of a signal involved in the initiation, maintenance or spread of cancerous growth may be evaluated in relevant conventional in vitro and in vivo assays. See e.g., Ishii et al., *J. Antibiot.* XLII:1877–1878 (1989) (in vitro evaluation of cytotoxic/antitumor activity); Sun et al, U.S. Pat. No. 5,206,249 (issued 27 Apr. 1993) (in vitro evaluation of growth inhibitory activity on cultured leukemia cells); and Sun et al, supra (xenograft models using various human tumor cell lines xenografted into mice, as well as various transgenic animal models).

Uses of the Compounds

Compounds of this invention may be used as biological reagents in assays as described herein for functional classification of an SH2 domain of a particular protein, particularly a newly discovered protein. Families or classes of SH2-bearing proteins may now be defined functionally, with respect to ligand specificity.

Moreover, compounds of this invention can be used to inhibit the occurrence of biological events resulting from molecular interactions mediated by an SH2 domain. This invention thus provides a method and reagents for inhibiting (totally or partially) the interaction between a protein containing an SH2 domain and a natural ligand thereto (i.e., a protein which normally binds in a cell to the SH2-bearing protein) or a biological activity mediated by such interaction. In this method, an SH2 binding or blocking compound of this invention is combined or contacted with the SH2 domain-containing protein, such as by introducing the compound into a cell in which the SH2-mediated interaction is to be inhibited. Following introduction of the compound, the interaction of the SH2 domain-bearing protein and its natural ligand is inhibited as may be readily detected. Inhibiting such interactions can be useful in research aimed at better understanding the biology of SH2-mediated events.

Such SH2 binding or blocking agents would be useful, for example, in the diagnosis, prevention or treatment of conditions or diseases resulting from a cellular processes mediated by an SH2-based interaction. For example, a patient can be treated to prevent the occurence or progression of osteoporosis or to reverse its course by administering to the patient in need thereof an SH2 binding or blocking agent which selectively binds Src SH2. There are many other conditions for which SH2 binding or blocking agents may be useful therapeutically, including breast cancer where the SH2 domain-containing proteins Src, PLCγ and Grb7 have been implicated. Other relevant conditions include prostate cancer, in which case targeting Grb2, PLCγ, and PI3K, all of which contain SH2 domains, may be useful in treatment or prevention of the disease. Inhibition of the interaction of Grb2 or Abl SH2 domains with Bcr-abl may be useful to treat chronic mylogenous leukemia (CML) or acute myelogenous leukemia (AML). Still other relevant applications of an SH2 inhibitor would be to prevent interferon-, growth factor-, or cytokine-mediated diseases (e.g. inflammatory diseases) by targeting the SH2 domains of STAT proteins. Agents that block the SH2 domains of ZAP-70, which is believed to be involved in activation of T-cells, would be useful in the treatment of autoimmune diseases. A compound that blocks one or both SH2 domains of ZAP-70 would also be useful as an immunosuppressant to prevent rejection of skin and organ transplants.

An SH2 binding or blocking agent of this invention can be formulated into a pharmaceutical composition containing a pharmaceutically acceptable carrier and/or other excipient(s) using conventional materials and means. Such a composition can be administered to an animal, either human or non-human, for therapy of a disease or condition resulting from cellular events involving an SH2-mediated molecular interaction. Administration of such composition may be by any conventional route (parenteral, oral, inhalation, and the like) using appropriate formulations as are well known in this art. The SH2 binding or blocking agent of this invention can be employed in admixture with conventional excipients, ie, pharmaceutically acceptable organic or inorganic carrier substances suitable for parenteral administration.

Pharmaceutical applications

By virtue of its capacity to inhibit protein-protein interactions required for cellular events of pharmacologic importance, a compound of this invention may be used in pharmaceutical compositions and methods for treatment or prevention in a mammal in need thereof.

Mammals include rodents such as mice, rats and guinea pigs as well as dogs, cats, horses, cattle, sheep, non-human primates and humans.

The preferred method of such treatment or prevention is by administering to a mammal an effective amount of the compound to prevent, alleviate or cure said disease or disorder. Such effective amounts can be readily determined by evaluating the compounds of this invention in conventional assays well-known in the art, including assays described herein.

Therapeutic/Prophylactic Administration & Pharmaceutical Compositions

The invention provides methods of treating, preventing and/or alleviating the symptoms and/or severity of a disease or disorder referred to above by administration to a subject of a in an amount effective therefor. The subject will be an animal, including but not limited to animals such as cows, pigs, chickens, etc., and is preferably a mammal, and most preferably human.

Various delivery systems are known and can be used to administer the SH2 inhibitor, e.g., encapsulation in liposomes, microparticles, microcapsules, etc. One mode of delivery of interest is via pulmonary administration, as detailed more fully infra. Other methods of introduction include but are not limited to intradermal, intramuscular, intraperitoneal, intravenous, subcutaneous, intranasal, epidural and oral routes. The SH2 inhibitor may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In specific embodiments, it may thus be desirable to administer the SH2 inhibitor locally to the area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

This invention also provides pharmaceutical compositions. Such compositions comprise a therapeutically (or prophylactically) effective amount of the SH2 inhibitor, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the SH2 inhibitor can also be accomplished topically by administering the compound(s) directly to the affected area of the skin of the individual. For this purpose, the SH2 inhibitor is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as antioxidants, humectants, viscosity stabilizers, and similar agents may be added as necessary.

In addition, in certain instances, it is expected that the SH2 inhibitor may be disposed within devices placed upon, in, or under the skin. Such devices include patches, implants, and injections which release the compound into the skin, by either passive or active release mechanisms.

Materials and methods for producing the various formulations are well known in the art [see e.g. U.S. Pat. Nos. 5,182,293 and 4,837,311 (tablets, capsules and other oral formulations as well as intravenous formulations)].

The effective dose of the SH2 inhibitor will typically be in the range of about 0.01 to about 50 mg/kgs, preferably about 0.1 to about 10 mg/kg of mammalian body weight, administered in single or multiple doses. Generally, the SH2 inhibitor may be administered to patients in need of such treatment in a daily dose range of about 1 to about 2000 mg per patient.

The amount of the SH2 inhibitor which will be effective in the treatment or prevention of a particular disorder or condition will depend on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level of the SH2 inhibitor, as the active component(s), should be determined by the attending physician or other health care provider and will depend upon well known factors, including route of administration, and the age, body weight, sex and general health of the individual; the nature, severity and clinical stage of the disease; and the use (or not) of concomitant therapies.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Pulmonary Administration

In one embodiment of this invention, the SH2 inhibitor is administered by pulmonary administration, e.g. via aerosolization. This route of administration may be particularly useful for treatment or prophylaxis of bronchial or pulmonary infection or tumors.

Pulmonary administration can be accomplished, for example, using any of various delivery devices known in the art (see e.g., Newman, S. P., 1984, in Aerosols and the Lung, Clarke and Davia (eds.), Butterworths, London, England, pp. 197–224; PCT Publication No. WO 92/16192 dated Oct. 1, 1992; PCT Publication No. WO 91/08760 dated Jun. 27, 1991; NTIS Patent Application 7-504-047 filed Apr. 3, 1990 by Roosdorp and Crystal), including but not limited to nebulizers, metered dose inhalers, and powder inhalers. Various delivery devices are commercially available and can be employed, e.g., Ultravent nebulizer (Mallinckrodt, Inc., St. Louis, Mo.); Acorn II nebulizer (Marquest Medical Products, Englewood, Colo.), Ventolin metered dose inhaler (Glaxo Inc., Research Triangle Park, North Carolina); Spinhaler powder inhaler (Fisons Corp., Bedford, Mass.) or Turbohaler (Astra). Such devices typically entail the use of formulations suitable for dispensing from such a device, in which a propellant material may be present.

Ultrasonic nebulizers tend to be more efficient than jet nebulizers in producing an aerosol of respirable size from a liquid (Smith and Spino, "Pharmacokinetics of Drugs in Cystic Fibrosis," Consensus Conference, Clinical Outcomes for Evaluation of New CF Therapies, Rockville, Md., Dec. 10–11, 1992, Cystic Fibrosis Foundation).

A nebulizer may be used to produce aerosol particles, or any of various physiologically acceptable inert gases may be used as an aerosolizing agent. Other components such as physiologically acceptable surfactants (e.g., glycerides), excipients (e.g., lactose), carriers, and diluents may also be included.

This invention is not to be limited in scope by the specific embodiments described herein. Indeed, various modifications of the invention in addition to those described herein will become apparent to those skilled in the art from the foregoing description. Such modifications are intended to fall within the the scope of the appended claims.

Various patents, patent applications and publications are cited herein, the disclosures of which are incorporated by reference in their entireties.

EXPERIMENTAL EXAMPLES

Unless specified otherwise, all moisture-sensitive reactions were performed in heat-dried glassware with magnetic stirring under an atmosphere of dry $N_2$. Acetone, benzene, EtOAc, hexane, $CH_3OH$, $CH_2Cl_2$, and THF were HPLC grade and used without purification. Workup means drying the organic extracts over anhydrous $MgSO_4$, filtration under reduced pressure, and concentration on a rotary evaporator. All chromatographic purification was performed using flash chromatography according to Still, W. C.; Kahn, M.; Mitra, A. *J. Org. Chem.* 1978, 43, 2923, unless otherwise noted.

I. Preparation of "-YB" moieties

The examples which follow disclose the synthesis of the following representative protected "-YB" molecules (and isomers thereof) comprising monocyclic moieties and fused heterocyclic systems containing two fused rings of 4 to 6 members each:

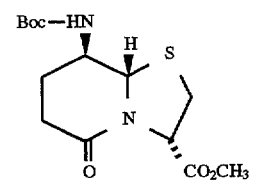
1(a)

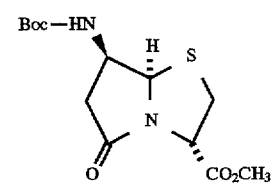
1(b)

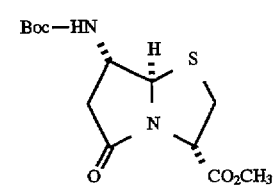
1(c)

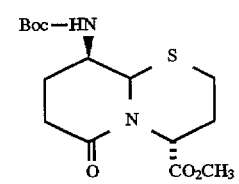
1(d)

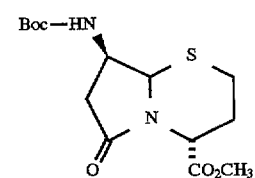
1(f, g)

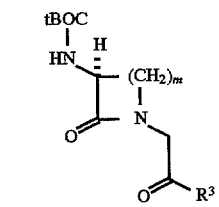
4(a)

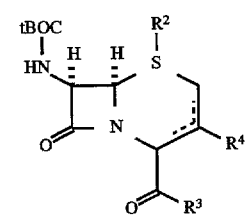
4(b)

-continued

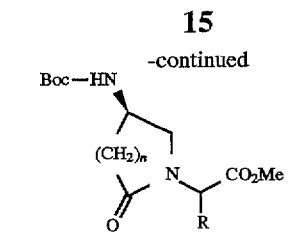

R = any amino acid side chain
n = 1 or 2

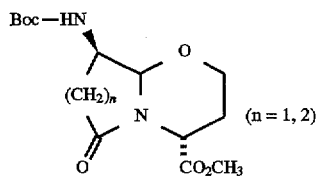

These moieties may be readily deprotected by conventional means to yield a free amine group for covalent attachment to an N-A-3,5-dinitrotyrosine moiety, where A is as defined above. Other ring systems bearing free amino or hydroxyl groups which may be covalently attached to an N-A-3,5-dinitrotyrosine moiety are known in the art.

Amino acids, dipeptides, tripeptides, oligopeptides may be obtained by conventional means, in free or protected form, for incorporation into compounds of this invention.

Synthesis of Compounds 1(a), 1(b), and 1(c)

Compounds 1(a), 1(b), and 1(c) can be prepared via Scheme I:

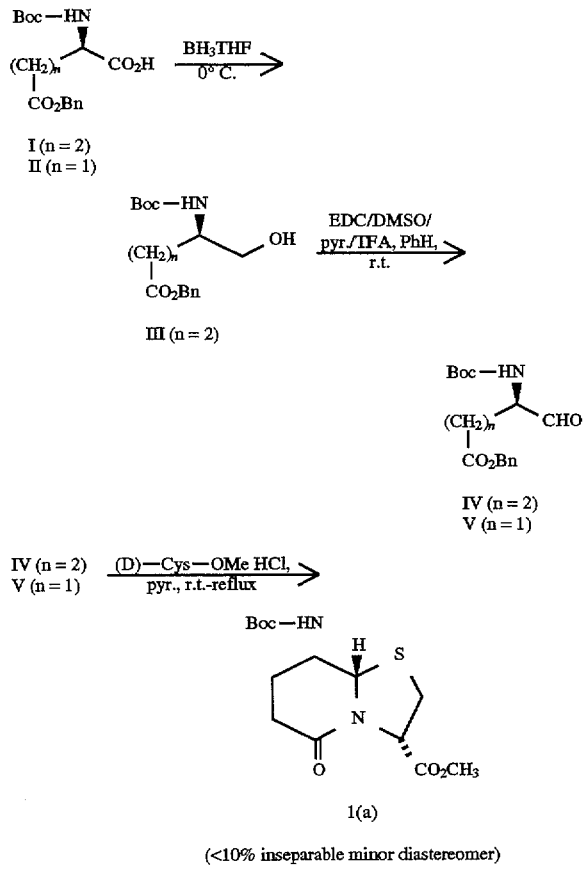

(<10% inseparable minor diastereomer)

-continued

[1(b):1(c), ~ 1:1]

The following procedure details the synthesis of compound 1(a). Compounds 1(b) and 1(c) can be prepared in an analogous fashion starting with Boc-D-Asp(OBzl)-OH (II).

To a cooled (0° C.) solution of Boc-D-Glu(OBzl)-OH (I) (3.0 g, 8.89 mmol) in 3.6 mL of THF was added 27.0 mL (26.7 mmol; 1.0M in THF) of $BH_3$.THF over 10 min via addition funnel. The resulting solution was stirred at 0° C. for 2 h, quenched with MeOH cautiously and dropwise, then stirred to ambient temperature. Concentration, dilution with MeOH, reconcentration, and a repeat of this process provided a thick residue, which was then diluted with brine and EtOAc. The separated aqueous layer was extracted with EtOAc and the combined organics worked up. Chromatography in 2:1 then 1:1 (hexane/EtOAc) provided 1.10 g of the alcohol III as a white solid:

$R_f$ 0.22 (1:1 hexanes/EtOAc); $^1$H NMR (acetone-$d_6$) δ 7.41–7.30 (m, 5H, —$C_6H_5$), 5.67 (br s, 1H, NHCO), 5.12 (s, 2H, $CH_2$Ph), 3.78 (m, 1H), 3.59–3.48 (m, 3H), 2.45 (m, 2H, $CH_2CO_2$), 1.97 (m, 1H), 1.74 (m, 1H), 1.40 (s, 9H, t-Bu).

A cloudy solution of alcohol III (2.39 g, 7.39 mmol) and 1-(3-dimethylaminopropyl)-3-ethylcarbodiimide hydrochloride (EDC; 8.44 g, 0.044 mol) in 18.0 mL of DMSO (anhydr.) and 50.0 mL of PhH was added 1.19 mL (0.015 mol) of pyridine (anhydr.) then 0.57 mL (7.39 mmol) of TFA. The cloudy solution was stirred at ambient temperature for 18 h, upon which the orange solution (some ppt) was cooled, added $H_2O$ and EtOAc, then diluted with brine. The separated aqueous layer was extracted with EtOAc and the combined organics washed with $H_2O$ then brine. Workup produced the aldehyde IV as a yellow-orange oil, which was used without purification in the next step:

$^1$H NMR (acetone-$d_6$) δ 9.57 (s, 1H, CHO) 7.41–7.30 (m, 5H, —$C_6H_5$), 6.44 (br s, 1H, NHCO), 5.13 (s, 2H, $CH_2$Ph), 4.04 (m, 1H), 2.52 (m, 2H, $CH_2CO_2$), 2.20 (m, 1H), 1.88 (m, 1H), 1.42 (s, 9H, t-Bu).

To a cooled (0° C.) solution of H-D-Cys-OH.HCl (2.0 g, 0.013 mol) in 89.0 mL of MeOH was added 4.5 mL (0.063 mol) of AcCl. The resulting colorless solution was heated at reflux for 5 h, cooled, concentrated on a rotary evaporator, and then stripped down with $Et_2O$ until a white solid resulted. Additional $Et_2O$ (~100 mL) was added, the solid filtered, washed with $Et_2O$, and excess solvent removed in vacuo to provide H-D-Cys-OMe.HCl as a white solid (1.80 g). The synthesized compound was identical ($^1$H NMR) to commercially available H-Cys-OMe.HCl (Sigma).

A solution of the crude aldehyde IV (7.39 mmol) and H-D-Cys-OMe.HCl (1.39 g, 8.13 mmol) in 50.0 mL pyridine (anhydr.) was stirred at ambient temperature for 2 days, then heated at reflux for 15 h. The resulting dark brown solution was cooled, concentrated, and diluted with saturated aqueous $NH_4Cl$ and EtOAc. The separated aqueous layer was extracted with EtOAc and the combined organics worked up. Chromatography in 5:1 (EtOAc/hexane) provided 0.740 g of compound 1(a) as a light brown solid, along with <10 % of an inseparable minor diastereomer. Recrystallization from acetone/hexane afforded crystals of compound 1(a) suitable for X-ray analysis:

HRMS (FAB+) calcd for $C_{14}H_{22}N_2O_5S$ (M+H)$^+$ 331.1328, found 331.1339.

Also, the stereochemistry in compounds 1(b) and 1(c) was determined by X-ray analysis of crystals obtained through recrystallization of the purified isomers from acetone/hexane:

Compound 1(b): HRMS (FAB+) calcd for $C_{13}H_{20}N_2O_5S$ (M+H)$^+$317.1171, found 317.1177.

Compound 1(c): HRMS (FAB+) calcd for $C_{13}H_{20}N_2O_5S$ (M+H)$^+$317.1171, found 317.1165.

Synthesis of the Molecules 1(d), 1(e), and 1(f, g)

Compounds 1(d), 1(e), and 1(f, g) can be prepared via Scheme II:

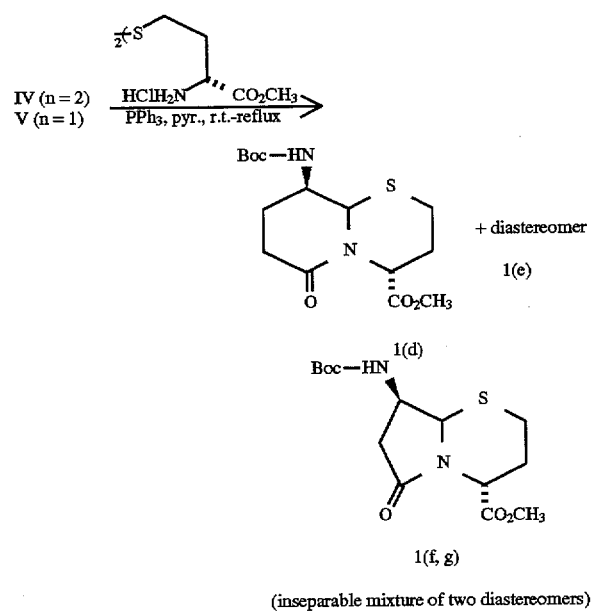

The following procedure details the synthesis of compounds 1(d) and 1(e). Compounds 1(f, g) can be prepared in an analogous fashion from the crude aldehyde V.

The derivatized amino acid D-homocystine methyl ester hydrochloride was prepared analogously to H-D-Cys-OMe.HCl starting with D-homocystine and using twice the equivalents of AcCl.

To a solution of the crude aldehyde IV (4.76 mmol) and D-homocystine methyl ester hydrochloride (0.967 g, 2.62 mmol) in 32.0 mL pyridine (anhydr.) was added 0.687 g (2.62 mmol) of Ph$_3$P. The yellow solution was stirred at ambient temperature for 2 days, then heated at reflux for 19 h, upon which the resulting dark brown solution was cooled, concentrated, and diluted with saturated aqueous NH$_4$Cl and EtOAc. The separated aqueous layer was extracted with EtOAc and the combined organics worked up. Chromatography in 2:1 (hexane/EtOAc) yielded 0.166 g of compound 1(d) as a light brown solid, in addition to 0.115 g of compound 1(e) also as a light brown solid:

Compound 1(d): HRMS (FAB+) calcd for $C_{15}H_{24}N_2O_5S$ (M+Na)$^+$367.1304, found 367.1296.

Compound 1(e): HRMS (FAB+) calcd for $C_{15}H_{24}N_2O_5S$ (M+H)$^+$345.1484, found 345.1494.

Synthesis of Compounds 2

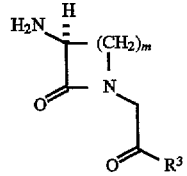

Compounds of formula 2, derivatives thereof and related compounds may be prepared by known procedures. See e.g. Hashimoto et al, 4-Unsubstituted azetidinone derivatives, U.S. Pat. No. 4207234; Curran et al, Preparation of (S)-[3-[[(2-amino-4-thiazolyl)-(Z)-methoxyiminoacetyl]amino]-2-oxo-1-azetidinylimino]acetates as antibacterial agents, U.S. Pat. No. 4,808,579; Skiles et al, Bioorg. Med. Chem. Lett. (1993), 3(4), 773–8; Schnorrenberg et al WO 9206998; Ede et al, Pept. Res. (1991), 4(3), 171–6; Thorsett, E. D., Actual. Chim. Ther. (1986), 13, 257–68; Thorsett et al, J. Med. Chem. (1986), 29(2), 251–60; and Freidinger et al, J. Org. Chem. (1982), 47(1), 104–9.

Synthesis of Compounds 3

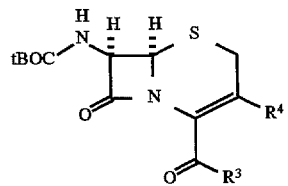

Compounds of formula 3 wherein $R^3$ is —OH and $R^4$ is —CH$_3$ or —CH$_2$O(CO)CH$_3$ may be prepared by known procedures or obtained from commercial sources. See e.g. the various references cited in the Merck Index for 7-aminocephalosporanic acid (Item 444) and Cephalosporin C (Item 1976). Related compounds can be prepared as previously described. See e.g. Teller et al, U.S. Pat. No. 3,926,984; Bohme et al, J. Org. Chem. (1973), 38(2), 230–6; and Ochiai et al, Tetrahedron Lett. (1972), (23), 2341–4.

Synthesis of Compounds 4(a)–(d)

The following illustrates a convenient synthetic approach to the four epimers of Z-BC-OMe (in which, Z: Carbobenzoxy, BC: Bicyclic moiety, Me: methyl):

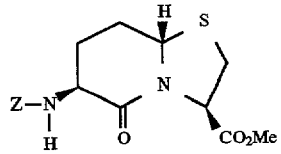

4(a) Z-L, L-BC—OMe

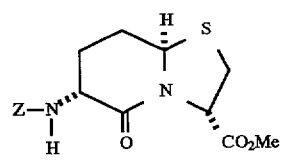

4(b) Z-D, D-BC—OMe

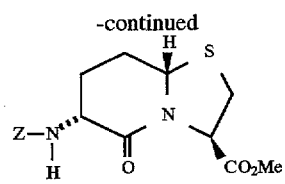

4(c) Z-D, L-BC—OMe

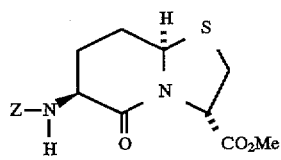

4(d) Z-L, D-BC—OMe

Scheme 1 illustrates the synthesis of Z-L,L-BC-OMe. The other epimers are prepared in a similar manner using the combination of stereoisomers of N-cbz-glutamic acid and cysteine methyl ester corresponding to the stereochemistry of the desired product. Any of Compounds 4(a) through 4(d) may be readily incorporated into the synthesis of other compounds of this invention through conventional deprotection and coupling steps. For instance, the N-cbz group may be routinely removed by classical procedures with trifluoroacetic acid/thioanisole, and the methyl ester may be conveniently removed with lithium hydroxide in methanol/water.

Scheme 1. The Preparation of Z-L, L-BC—OMe

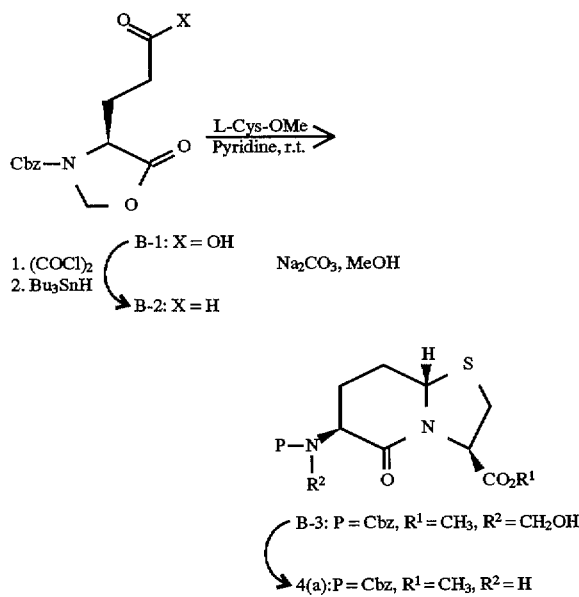

Thus, the oxazolidinone B-1, which is formed from N-Cbz-L-glutamic acid by heating with paraformaldehyde in benzene in the presence of catalytic amount of p-toluenesulfonic acid, is treated with oxalyl chloride followed by reduction of the acid chloride with n-Bu$_3$SnH to give the aldehyde B-2. Condensation of the aldehyde with L-cysteine methyl ester in pyridine over a 5-day period gives the bicyclic, hydroxymethyl derivative B-3. The hydroxymethyl group is removed under mildly alkaline conditions to provide the Cbz-protected methyl ester 4(a) (Z-L,L-BC-OMe).

(S)-3-Carbobenzoxy-5-oxo-4-oxazolidinepropanal, B-2.

Z-L-Glutamic acid (25 g, 88.7 mmol) was heated with paraformaldehyde (5.33 g, 2 eq) and p-toluenesulfonic acid monohydrate (1.0 g, 6 mol %) in benzene (500 mL) at reflux for 1.5 h, with removal of water by a Dean-Stark trap. The reaction mixture was then cooled to r.t. and 100 mL of EtOAc was added. The solution was washed with water (2×250 mL), sat'd brine (200 mL), dried (MgSO$_4$), and concentrated to give 26.0 g (100%) of a colorless oil as the oxazolidinone B-1.

TLC R$_f$ 0.58 (9:1:0.1 CHCl$_3$/MeOH/AcOH). $^1$H-NMR (CDCl$_3$, 300 MHz): 7.37 (m, 5H, C$_6$H$_5$—), 5.54 (br. s, 1H, 2-H$_a$), 5.23 (d, 1H, J=4.4 Hz, 2-H$_b$), 5.19 (s, 2H, benzyl CH$_2$), 4.41 (t, 1H, J=5.8 Hz, 4-H), 2.51 (br. s, 2H, 7-H), 2.32 (m, 1H, 6-H$_a$), 2.21 (m, 1H, 6-H$_b$).

A solution of the acid B-1 (26.0 g, 88.7 mmol) in CH$_2$Cl$_2$ (250 mL) was treated with (COCl)$_2$ (15.5 mL, 2 eq) in the presence of catalytic amount of DMF (0.20 ml, 4 mol %) at r.t. for 14 h. The reaction mixture was evaporated to a colorless oil and the crude acid chloride was redissolved in anhydrous EtOAc (600 ml). Bu$_3$SnH (25.8 g, 1.0 eq) was added with stirring via a syringe pump at 0° C. under N$_2$ over a 1.5 h period and the resulting solution was allowed to warm from 0° C. to r. t. for 14 h. The mixture was concentrated under reduced pressure and the oil was dissolved in 500 mL of CH$_3$CN. The CH$_3$CN solution was washed with petroleum ether (5×200 mL) and then concentrated to give 24.5 g (100%) of the aldehyde as a yellowish oil that carried on without purification.

TLC R$_f$ 0.55 (1:1 EtOAc/Hexanes). $^1$H-NMR (CDCl$_3$, 300 MHz): 9.65 (s, 1H, —CHO), 7.30 (m, 5H, C$_6$H$_5$—), 5.46 (s, 1H, 2-H$_a$), 5.12 (m, 3H, 2-H$_b$ and benzyl CH$_2$), 4.30 (m, 1H, 4-H), 2.50 (m, 2H, 7-H), 2.25 (m, 2H, 6-H). Z-L,L-BD-OMe, 4(a).

L-Cys-OMe (15.2 g, 88.7 mmol) was added in one portion to a stirring solution of the crude aldehyde B-2 (24.5 g, 88.7 mmol) in pyridine (600 mL, anhydrous) at r.t. under N$_2$ and the resulting clear solution was left to stand at r.t. for 5 d. The solvent was evaporated under reduced pressure to give a yellow oil, which was dissolved in 500 mL of EtOAc. The resulting cloudy solution was washed with sat'd NH$_4$Cl (500 mL), H$_2$O (250 mL), and sat'd brine (250 mL), dried (MgSO$_4$), and evaporated to yield a yellow oil. Chromatography (silica gel, EtOAc/hexanes gradient) gave 20.6 g (59%) of pure condesation product, N-hydroxymentyl-Z-L, L-BC-OMe, 4(a) as a white foam.

TLC R$_f$ 0.47 (9:1 CHCl$_3$/MeOH). $^1$H-NMR (CDCl$_3$, 300 MHz): 7.30 (m, 5H, C$_6$H$_5$—), 5.14 (s, 2H, benzyl CH$_2$), 5.20–4.20 (m, 5H, 2,5,8-H and O—CH$_2$—N), 3.68 (s, 3H, OMe), 3.29 (m, 1H, 3-H$_a$), 3.15 (m, 1H, 3-H$_b$), 2.40–2.10 (m, 3H, 7-H$_a$,H$_b$, 6-H$_a$), 1.80 (m, 1H, 6H$_b$). $^{13}$C-NMR (CDCl$_3$, 75 MHz): 170.0, 167.8, 155.3, 136.1, 128.6, 128.4, 128.0, 68.1, 67.6, 62.6, 61.3, 53.9, 52.7, 31.6, 28.1, 26.5.

A solution of the bicyclic dipeptide B-3 (20.6 g, 52.3 mmol) in anhydrous MeOH (200 mL) was stirred with solid Na$_2$CO$_3$ (3.9 g, 0.7 eq) at r.t. for 4 h. The reaction was evaporated and the crude product was chromatographed (silica gel, EtOAc/Hexanes gradient) to give 12.5 g (67%) of a white solid.

TLC: R$_f$ 0.36 (1:1 EtOAc/Hexanes). $^1$H-NMR (CDCl$_3$, 300 MHz): d7.28 (m, 5H, C$_6$H$_5$—), 5.44 (br. s, 1H, NH), 5.23 (m, 3H, benzyl CH$_2$, and 2-H), 4.86 (m, 1H, 5-H), 4.14 (m, 1H, 8-H), 3.70 (s, 3H, OMe), 3.30 (dd, 1H, J=11.2, 8.0 Hz, 3-H$_a$), 3.09 (dd, 1H, J=11.2, 5.8 Hz, 3-H$_b$), 2.55 (m, 1H, 7-H$_a$), 2.30 (m, 1H, 6H$_a$), 1.82 (m, 2H, 7-H$_b$, 6-H$_b$). $^{13}$C-NMR (CDCl$_3$, 75 MHz): 170.3, 167.1, 156.4, 136.2, 128.3, 127.9, 127.8, 66.7, 62.7, 60.5, 52.8, 51.8, 31.7, 27.8, 27.5.

Synthesis of Monocyclic Moieties

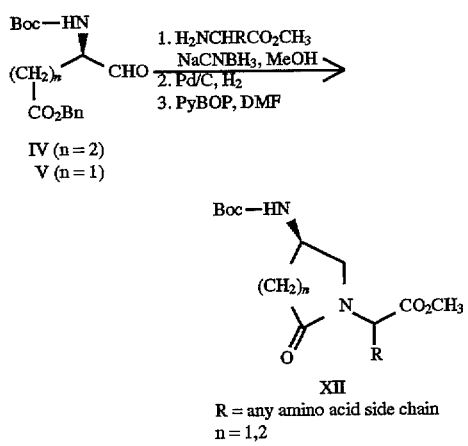

R = any amino acid side chain
n = 1,2

The monocyclic compounds XII can be synthesized from aldehydes IV and V. Reductive amination with a derivatized amino acid following the method of Borch, R. F. et al *J. Am. Chem. Soc.* 1971, 93, 2897, followed by catalytic hydrogenation and cyclic amide formation can provide XII.

Synthesis of an Oxygen-containing Bicyclic Moiety

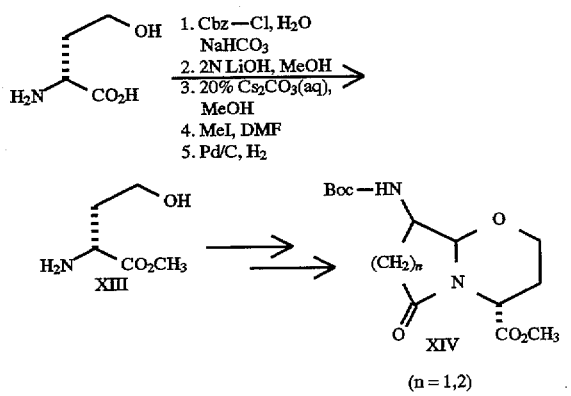

(n = 1,2)

D-homoserine methyl ester XIII can be synthesized from D-homoserine by first forming the Cbz carbamate using standard conditions (Bodanszky, A. et al *The Practice of Peptide Synthesis* (1984), p.14). Hydrolysis of the generated lactone, formation of the methyl ester (Wang, S.-S. et al *J. Org. Chem.* 1977, 42, 1286), and catalytic hydrogenation can provide D-homoserine methyl ester XIII. Coupling with aldehydes IV and V as previously described can afford spacer XIV.

II. Preparation of N-substituted 3,5-dinitrotyrosines

N-Fmoc-3,5-dinitro-L-tyrosine

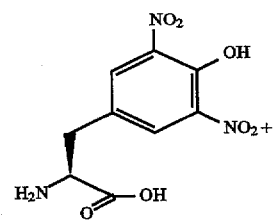

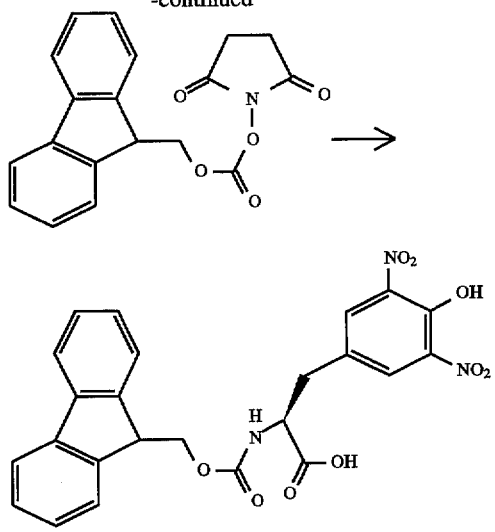

Synthesis was carried out as follows (descriptions of using Fmoc-OSu to protect the alpha-amino group of amino acids with Fmoc can be found in A. Paquet (1982) Can. J. Chem. 60, 976). 1.5 g of 3,5-Dinitro-L-tyrosine monohydrate (Aldrich) was added to 200 mls deionized $H_2O$, with 6.6 mls of 10% $Na_2CO_3$. Solution was stirred until a clear yellow solution was obtained. pH was adjusted to approximatly 7 using small portions of 10% $Na_2CO_3$. 200 mls of dimethoxy ethane (DME) was added to above with stirring. 1.1 eq. (1.9 g) of Fmoc-OSu was dissolved in a minimum amount of DME. This Fmoc-OSu solution was added dropwise to the solution of dinitro-L-tyrosine with stirring. The reaction was carried out overnight with stirring at room termperature.

The next morning, the completion of the reaction was judged to be greater than 95% by TLC, and DME was removed by rotory evaporation under reduced pressure at 40 deg. The reaction mixture was extracted 3× with dietheyl ether, and excess ether is removed by rotory evaporation under reduced pressure (at room temp.) The reaction mixture was acidified to pH 2–3 using 10% $KHSO_4$. A whitish-yellow precipitate formed. The reaction mixture left overnight in a 4 deg. refrigerator.

The next morning the precipitate was vacuum filtered using a buchner funnel (number 1 Whatman filter paper). The filtrate was resuspended and washed 3× with small portions of ice-cold 0.1N HCl, and then 2× with ice-cold deionized water. The filtrate was dried overnight under vacuum with $P_2O_5$ as a dessicant.

Yield was 2.55 g, 96% by weight. FAB MS measured [M−H]=492; calc $C_{24}H_{18}N_3O_9$ =492.

N-Fmoc-3-nitro-L-tyrosine may be prepared as described above but substituting 3-nitro-L-tyrosine for 3,5-dinitro-L-tyrosine.

III. Covalent attachment of 3,5-dinitrotyrosine derivatives to -YB moieties 3,5-Dinitrotyrosine-YB compounds may be obtained by the following route:

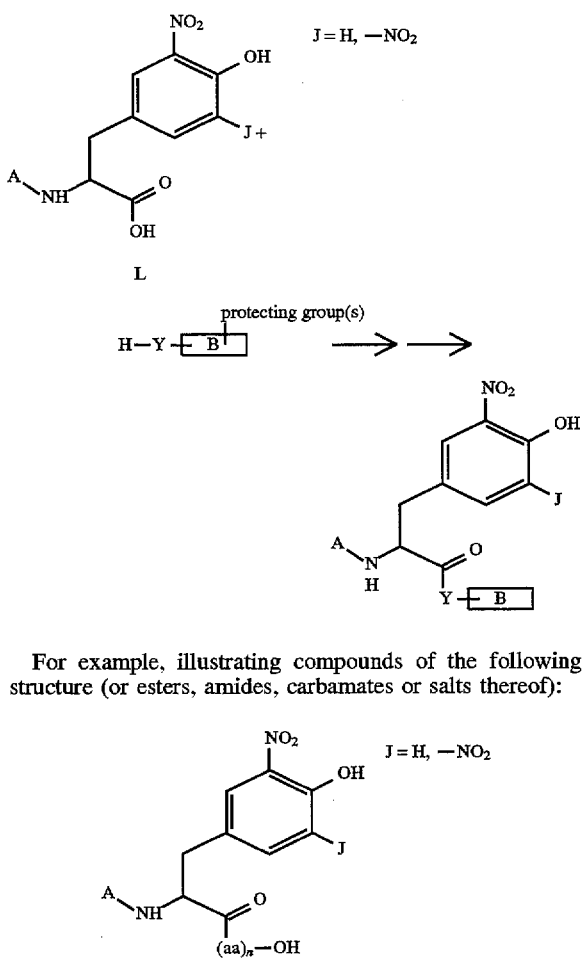

For example, illustrating compounds of the following structure (or esters, amides, carbamates or salts thereof):

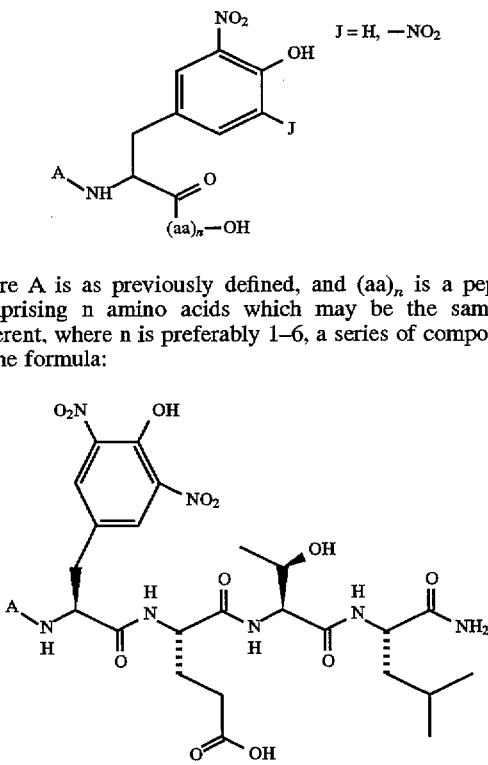

where A is as previously defined, and (aa)$_n$ is a peptide comprising n amino acids which may be the same or different, where n is preferably 1–6, a series of compounds of the formula:

with various "A" groups were synthesized as described below.

Methodology:

In general, synthesis was carried out in a manual peptide synthesis apparatus as follows: 100 mgs of Fmoc-Rink amide resin (4-(2',4'-Dimethoxyphenyl-Fmoc-aminomethyl) phenoxy resin; Advanced Chemtech) with substitution levels of 0.3–0.6 mmole/g was added to a polypropylene chromatography column (PD-10, Pharmacia Inc.) with a porous frit above a leur tip, and with a silicone cap. The column reaction vessels were fixed to a rotary shaker, and 5 ml of dimethylacetamide (DMA) was added, and the vessels were shaken for 20 min. to swell the resin. The sequential cycles of removal of the Fmoc, washing, coupling of the incoming, activated Fmoc-amino acid, and washing were done as described in table 1 below. Reagents and solvent used are N-methylpyrrolidone (NMP), 2-(1H-Benzotriazole-1-yl)-1,1,3,3-tetramethyluronium tetrafluoroborate (TBTU), and N-methyl morpholine (NMM). Each cycle below consists of adding solvent and/or reagent to the moist resin, shaking the resultant slurry, and vacuum evacuating the reaction vessel of liquid, leaving moist resin behind.

TABLE 1

| Cycle | Description | Reagent | Repeats |
|---|---|---|---|
| 1 | Deprotection | 20% Piperidine/DMA | 2x 20 min |
| 2 | Wash | DMA | 5x 1 min |
| 3 | Wash | NMP | 1x 1 min |
| 4 | Coupling | 4x AA (or acid):4x TBTU: 8x NMM in NMP | 1x 120 min. |
| 5 | Wash | NMP | 1x 1 min |
| 6 | Wash | DMA | 5x 1 min |

Amino acids (AA) used for this series of compounds included Fmoc-LeuOH, Fmoc-Thr(tBu)OH, Fmoc-Glu(tBu) OH, Fmoc-PheOH, Fmoc-D-PheOH, Fmoc-2-NalOH, Fmoc-1-NalOH, Fmoc-IleOH, Fmoc-AlaOH, Fmoc-Asp (tBu)OH, Fmoc-ValOH, Fmoc-GlyOH, and Fmoc-Asn(Trt) OH. Coupling was initiated by adding solid Fmoc-amino acid to moist resin at the beginning of step 4, followed by adding NMP, NMM, and solid TBTU.

After coupling of Fmoc-dinitro tyrosine, and removal of the Fmoc from the peptide chain, any of a series of acids were coupled to the N-terminus of the dnY containing peptide (step 4, table 1) using the methodology above for amino acids. Washes were done as in steps 5 and 6, table 1 and the synthesis was completed by washing the peptide-resin 3× with CH$_2$Cl$_2$, and 3× with methanol (MeOH). Moist resins were desiccated overnight under vacuum with P$_2$O$_5$ as a dessicant.

Cleavage and Deprotection:

Dry resins (100–200 mg) were cleaved using a reaction mixture containing trifluoroacetic acid (TFA), ethane dithiol (EDT), and H$_2$O, in a ratio of 90:5:5 respectively, for 2 h, followed by filtration of the supernatant through a plug of glass wool, and a secondary cleavage of the resin using 90% TFA/H$_2$O, for 30 min. Resin and supernatant were filtered and washed with two small portions of 90% TFA/H$_2$O. The resin was discarded, and the supernatant, containing the cleaved, deprotected peptide, was kept. TFA was evaporated from the peptide solution using a stream of dry N$_2$ gas, until a slurry remained. Approximately 4–5 ml of H$_2$O was added to the peptide slurry, and it was suspended with sonication in a water bath. This material was extracted 3 times with ice-cold diethyl ether. The ether layers were discarded, and remaining ether in the crude peptide solution was rotary evaporated under reduced pressure. The crude solutions were then lyophilized overnight on a Virtis lyophilizer, yielding a crude peptide powder. Purification and Characterization:

Crude peptides were analyzed by reverse phase HPLC on an HP 1050 gradient HPLC system, equipped with a diode array UV/Vis detector. All analytical HPLC experiments were done using a 4.6 mm diameter Vydac C18 reverse phase column, utilizing a gradient of 5–65% CH₃CN in H₂O with 0.1% TFA, from 2–32 min. Elution was monitored at 220 and 265 nm. Purification of peptides was performed on a 10 mm Vydac C18 reverse phase column, utilizing gradients of increasing amounts of CH₃CN (increasing from 0.5 to 1.0% min.) with 0.1% TFA, at a flow rate of 3 ml/min.

Crude peptide was solubilized using the minimal amount of 90% DMSO/H₂O required to achieve a clear solution. Generally concentrations of crude peptide solution was in the range of 40–100 mg/ml. A series of sequential purification runs were performed, injecting 15–35 ul of peptide solution per run (0.6–3.5 mg/injection). The central portion of the desired peak was collected and lyophilized overnight on a Virtis lyophilizer.

Analysis of Purified Peptide:

Purified peptide was analyzed for purity by analytical reverse phase HPLC (as above), utilizing the diode array detector to check for purity of individual peaks. Identity of the peptides was confirmed by FAB MS.

DVL-resin, the peptide is cleaved, deprotected, lyophilized and analyzed as described. Analytical HPLC of purified product >90% pure. FAB MS, found [M−H]-, 818, calc C₃₉H₄₄N₇O₁₃, 818.

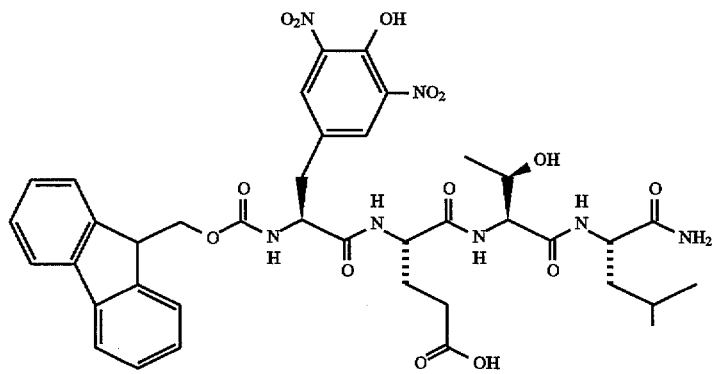

Compound 5 [SEQ ID NO:1]

Synthetic methods are those described in the general methods description. After coupling of Fmoc-dnYOH to the ETL-resin, the peptide is cleaved, deprotected, lyophilized and analyzed as described. Analytical HPLC of purified product >90% pure. FAB MS, found [M−H]-, 834, calc C₃₉H₄₄N₇O₁₄, 834.

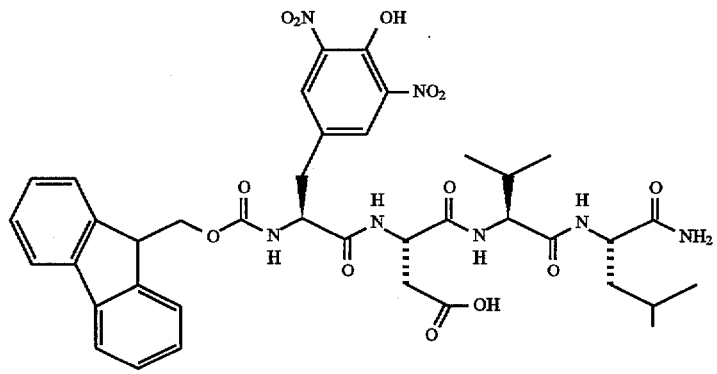

Compound 6:[SEQ ID NO:2]

Synthetic methods are those described in the general methods description. After coupling of Fmoc-dnYOH to the

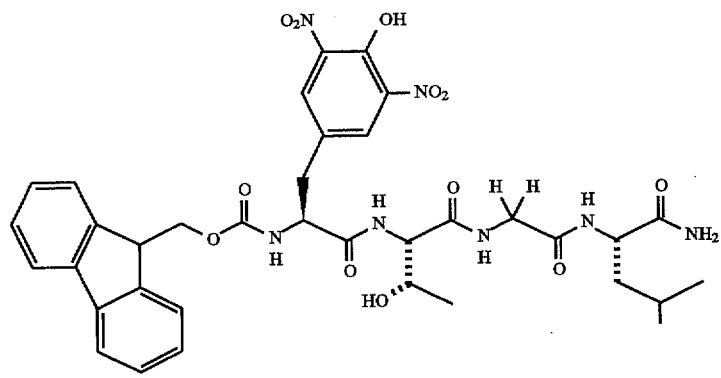

Compound 7 [SEQ ID NO:3]

Synthetic methods are those described in the general methods description. After coupling of Fmoc-dnYOH to the TGL-resin, the peptide is cleaved, deprotected, lyophilized and analyzed as described. Analytical HPLC of purified product >90% pure. FAB MS, found [M–H]-, 762, calc $C_{36}H_{40}N_7O_{12}$, 762.

was removed from the N-terminal dnY residue using the standard 20% piperidine treatment (table 1). After washing as above, coupling of 9-fluoreneacetic acid (Aldrich) was carried out using 4× equivalents of the acid, 4× equivelents of TBTU, and 8× equivalents of NMM. Washing, cleavage/deprotection and purification all occured as above. By

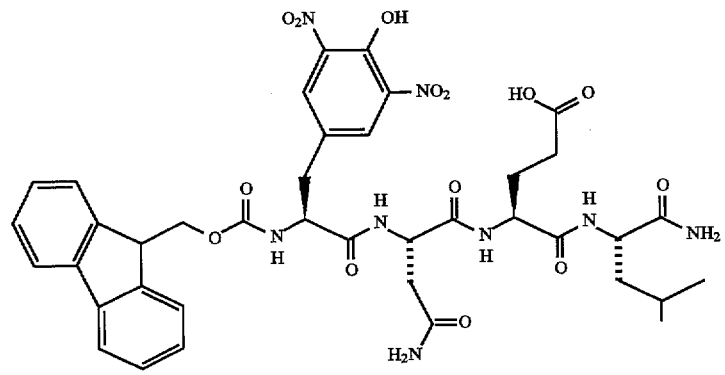

Compound 8:[SEQ ID NO:4]

Synthetic methods are those described in the general methods description. After coupling of Fmoc-dnYOH to the NEL-resin, the peptide is cleaved, deprotected, lyophilized and analyzed as described. Analytical HPLC of purified product >90% pure. FAB MS, found [M–H]-, 847, calc $C_{39}H_{43}N_8O_{14}$, 847.

HPLC, purity was >90%. FAB MS, found [M–H]-, 818, calc $C_{39}H_{44}N_7O_{13}$, 818.

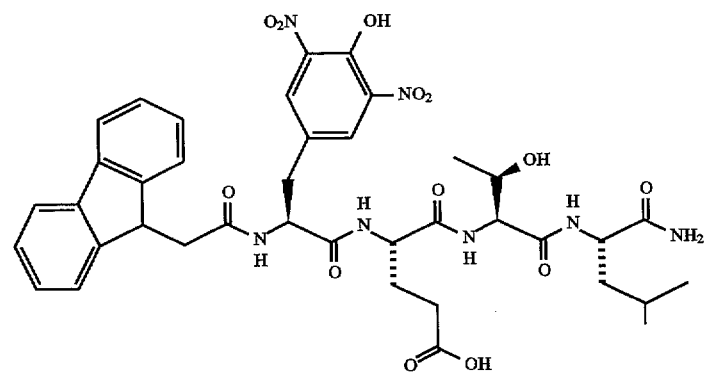

Compound 9.[SEQ ID NO:5]

Synthesis was carried out as described above. After synthesis of dnY-ETL on the Rink resin, the N-terminal Fmoc Compound 10.[SEQ ID NO:6]

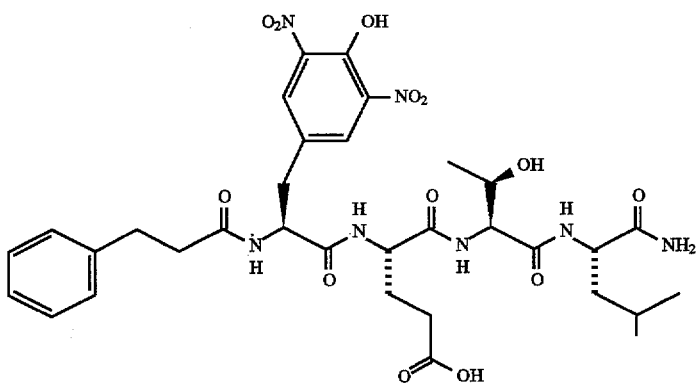

Synthesis, cleavage/deprotection and purification was carried out as described for compound 9. Final coupling used 3-phenyl propionic acid (Aldrich) to dnYETL on Rink resin. By HPLC, purity was >90%. FAB MS, found [M–H]-, 744, calc $C_{33}H_{41}N_7O_{13}$, 818.

1-naphthylacetic acid (Aldrich) to dnYETL on Rink resin. By HPLC, purity was >90%. FAB MS, found [M–H]-, 780, calc $C_{36}H_{42}N_7O_{13}$, 780.

Compound 11.[SEQ ID NO:7]

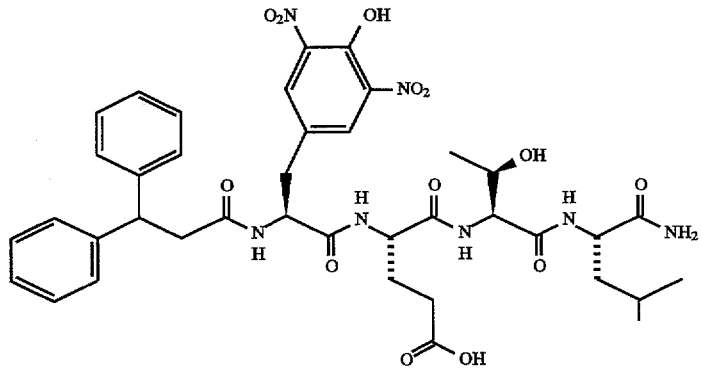

Synthesis, deprotection and purification was carried out as described for compound 9. Final coupling used 3,3-diphenylpropionic acid (Aldrich) to dnYETL on Rink resin. By HPLC, purity was >90%. FAB MS, found [M–H]-, 820, calc $C_{33}H_{42}N_7O_{13}$, 820.

Compound 12.[SEQ ID NO:8]

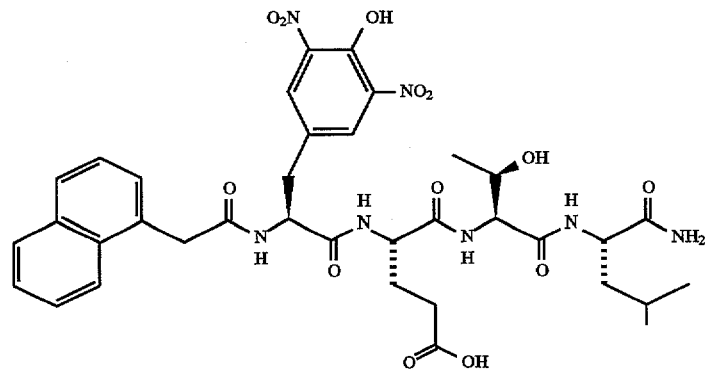

Synthesis, deprotection and purification was carried out as described for compound 9. Final coupling used Compound 13.[SEQ ID NO:9]

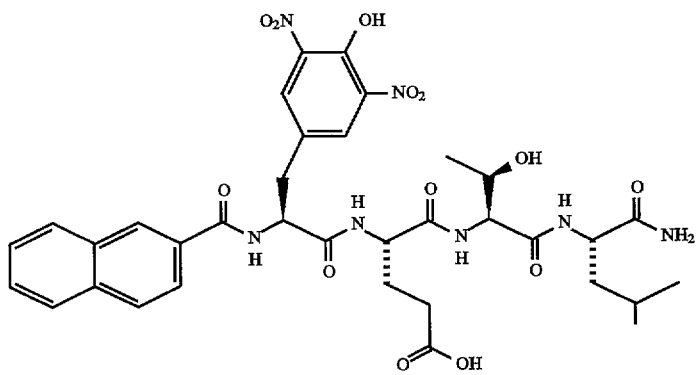

Synthesis, deprotection and purification was carried out as described for compound 9. Final coupling used 1-naphthoic acid (Aldrich) to dnYETL on Rink resin. By HPLC, purity was >90%. FAB MS, found [M–H]-, 766, calc $C_{35}H_{40}N_7O_{13}$, 766.

Aromatic Amino Acid Caps ("A")
General Synthesis.

The general synthetic method is that described above for the aromatic acid caps, with minor changes. After coupling of the Fmoc-amino acids to the N-terminus of the dnY- Compound 14:[SEQ ID NO:10]

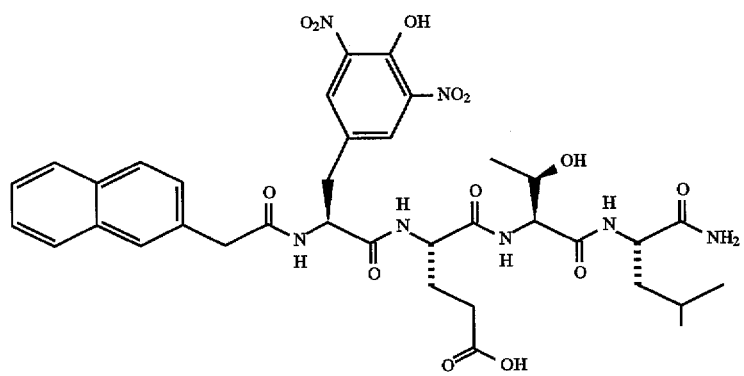

Synthesis, deprotection and purification was carried out as described for compound 9. Final coupling used 2-naphthylacetic acid (Aldrich) to dnYETL on Rink resin. By HPLC, purity was >90%. FAB MS, found [M–H]-, 780, calc $C_{36}H_{42}N_7O_{13}$, 780.

peptide on the resin, the Fmoc group was removed with standard methods, and after washing, the peptide was acylated using 0.5M acetic anhydride, 0.5M pyridine in DMA, for 20 min. This was followed by standard washings, and cleavage/deprotection of the peptide from the resin. Crude Compound 15:[SEQ ID NO:11]

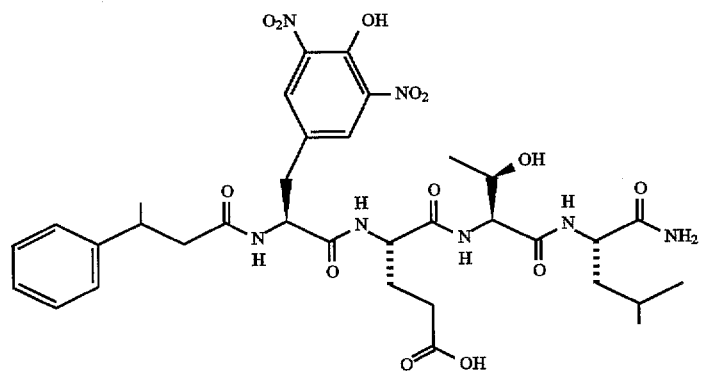

Synthesis, deprotection and purification was carried out as described for compound 9. Final coupling used 3-methyl, 3'-phenyl propionic acid (Aldrich) to dnYETL on Rink resin. By HPLC, purity was >90%. FAB MS, found [M–H]-, 756, calc $C_{34}H_{44}N_7O_{13}$, 756.

lyophilized peptide was treated with 1–300 ul of conc. $NH_4$ OH for 30 min. with sonicating (to cleave any ester of the dnY hydroxyl). The $NH_4$ OH was removed with a stream of dry $N_2$ gas, and crude product was dissolved in an excess of $H_2O$, frozen and lyophilized. Purification and characterization were as above.

Compound 16:

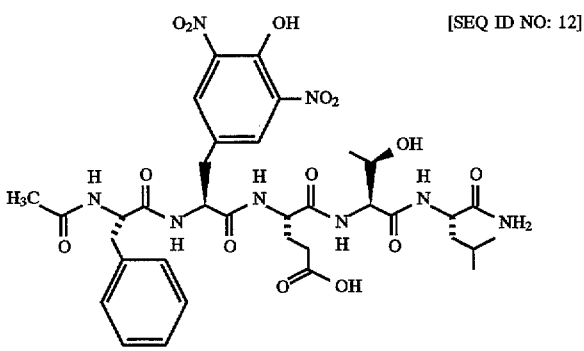

[SEQ ID NO: 12]

Synthesis, deprotection and purification was carried out as described above. Final coupling used Fmoc-L-PheOH to dnYETL on Rink resin, followed by removal of the Fmoc, acylation and standard processing. By HPLC, purity was >90%. FAB MS, found [M–H]-, 801, calc $C_{35}H_{45}N_8O_{14}$, 801.

Compound 17:

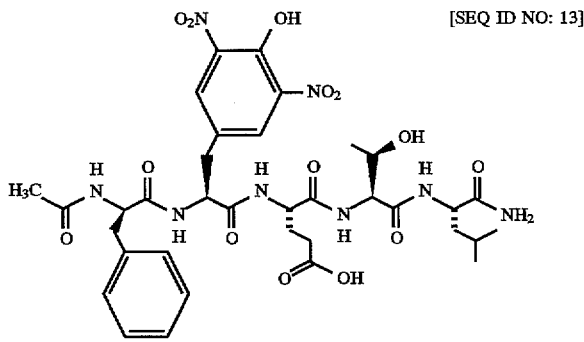

[SEQ ID NO: 13]

Synthesis, deprotection and purification was carried out as described for compound 16. Final coupling used Fmoc-D-PheOH to dnYETL on Rink resin, followed by removal of the Fmoc, acylation and standard processing. By HPLC, purity was >90%. FAB MS, found [M–H]-, 801, calc $C_{35}H_{45}N_8O_{14}$, 801.

Compound 18:

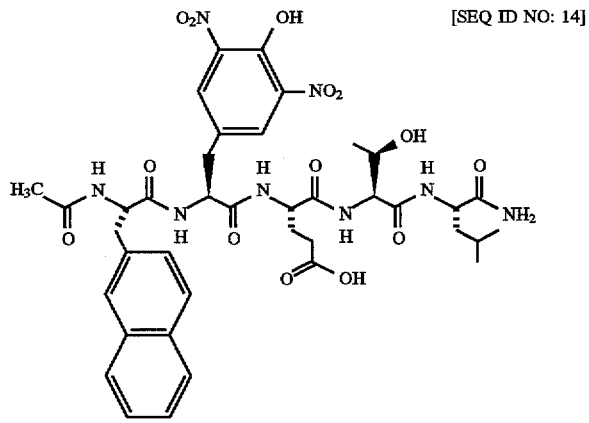

[SEQ ID NO: 14]

Synthesis, deprotection and purification was carried out as described for compound 16. Final coupling used Fmoc-2-NalOH (Fmoc-2-Naphthylalanine) to dnYETL on Rink resin, followed by removal of the Fmoc, acylation and standard processing. By HPLC, purity was >90%. FAB MS, found [M–H]-, 851, calc $C_{39}H47N_8O_{14}$, 851.

Compound 19:

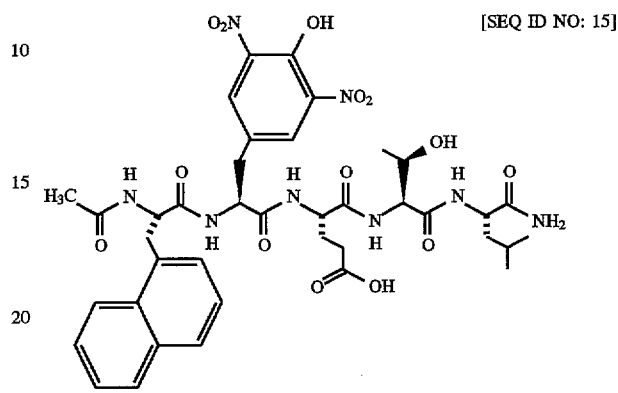

[SEQ ID NO: 15]

Synthesis, deprotection and purification was carried out as described for compound 16. Final coupling used Fmoc-1-NalOH (Fmoc-1-Naphthylalanine) to dnYETL on Rink resin, followed by removal of the Fmoc, acylation and standard processing. By HPLC, purity was >90%. FAB MS, found [M–H]-, 851, calc $C_{39}H_{47}N_8O_{14}$, 851.

Compounds in which J=H:

Compound 20:

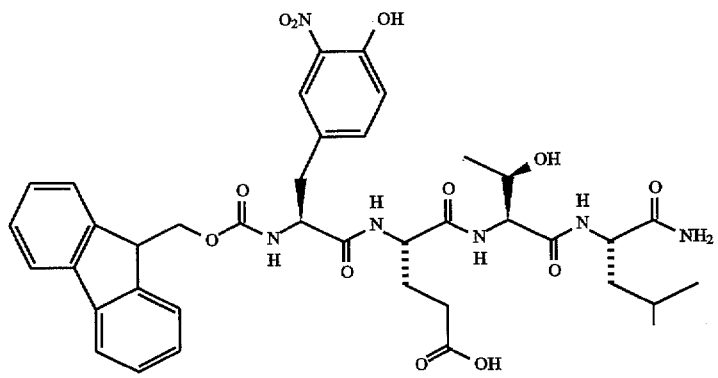

[SEQ ID NO: 16]

Synthesis, deprotection and purification was carried out as in the general methods, and as described for compound 5, with minor changes. Fmoc-mononitro-tyrosine (Bachem) was coupled to the ETL-resin. The peptide was cleaved as described, deprotected, lyophilized, purified and analyzed. Analytical HPLC of purified product, >90% pure. FAB MS, found [M−H]−, 789; calc. $C_{39}H_{46}N_6O_{12}$, 789.

Compound 21:

[SEQ ID NO: 17]

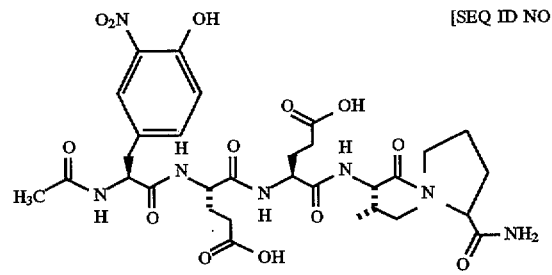

Synthesis, deprotection and purification was carried out as in the general methods, with minor changes. Fmoc-mononitro-tyrosine was coupled to the EEIP-resin. The Fmoc was removed as described in table 1, and the N-terminal amino group was acylated as with compounds 16–19. The peptide was cleaved as described, deprotected, lyophilized, purified and analyzed. Analytical HPLC of purified product, >90% pure. FAB MS, found [M−H]−, 734; calc. $C_{32}H_{45}N_7O_{13}$, 734.

Synthesis of Compounds 1(h), 1(i), 1(j), and 1(k)

Compounds 1(h), 1(i), 1(j), and 1(k) can be prepared via Scheme III:

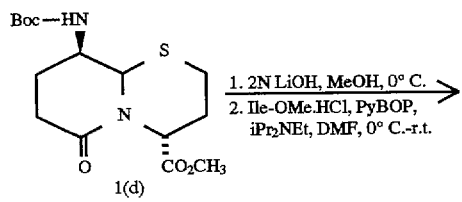

1(d)

1. 2N LiOH, MeOH, 0° C.
2. Ile-OMe.HCl, PyBOP, iPr₂NEt, DMF, 0° C.-r.t.

-continued

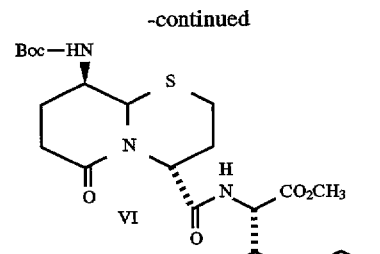

VI $$VI \xrightarrow[\text{2. N-Fmoc-3,5-dinitro-L-Tyr}_2\text{—OH}]{1.\ TFA/CH_2Cl_2(1:1),\ r.t.}$$
PyBOP, iPr₂NEt, DMF, 0° C.-r.t.

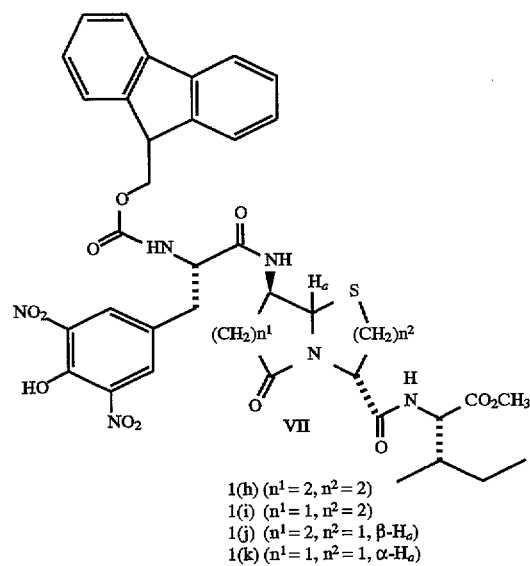

VII

1(h) (n¹ = 2, n² = 2)
1(i) (n¹ = 1, n² = 2)
1(j) (n¹ = 2, n² = 1, β-Hₐ)
1(k) (n¹ = 1, n² = 1, α-Hₐ)

$$1(f,g) \xrightarrow[\text{2. Ile-OMe.HCl, PyBOP,}]{1.\ 2N\ LiOH,\ MeOH,\ 0°\ C.}$$
iPr₂NEt, DMF, 0° C.-r.t.

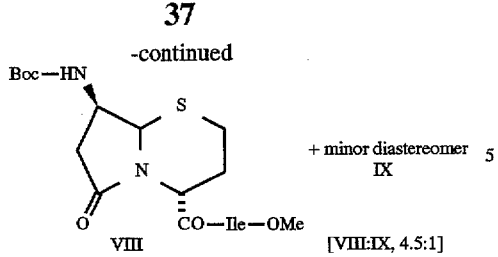

+ minor diastereomer
IX

[VIII:IX, 4.5:1]

The following procedure details the synthesis of compound 1(h). Compounds 1(i), 1(j), and 1(k) can be prepared in an analogous fashion from the spacer molecules 1(f, g), 1(a), and 1(b), respectively.

To a cooled (0°) solution of 0.163 g (0.47 mmol) of methyl ester 1(d) in 2.5 mL of MeOH was added 0.70 mL (1.42 mmol) of a 2N LiOH (aq) solution. The yellow solution was stirred at 0° for 4.5 h, upon which it was diluted with 5–10 mL $H_2O$, acidified with conc. HCl to pH=1–2, and the aqueous layer extracted with EtOAc. Workup provided the carboxylic acid as a light brown solid, which was used without purification in the next step.

A cooled (0°) flask containing the crude carboxylic acid (0.47 mmol) and 0.246 g (0.47 mmol) of benzotriazole-1-yl-oxy-tris-pyrrolidino-phosphoniumhexafluorophosphate (PyBOP) was added 0.75 mL of DMF (anhydr.) and the yellow solution stirred at 0° for ~10min. The solution was transferred via syringe with dropwise addition to a cooled (0°) solution of H-Ile-OMe.HCl (0.072 g, 0.39 mmol) in 0.15 mL of DMF. To this was added 0.25 mL (1.42 mmol) of N,N-diisopropylethylamine and the solution stirred to ambient temperature overnight (13 h). The yellow solution was concentrated to a thick residue via short-path distillation (40°/in vacuo), then diluted with EtOAc and washed successively with 5% aqueous citric acid, saturated aqueous $NaHCO_3$, $H_2O$, and brine. Workup followed by chromatography in 2:1(hexane/EtOAc) yielded the coupled product VI (0.146 g) as a white solid.

A solution of compound VI (0.080 g, 0.17 mmol) in 1.0 mL $CH_2Cl_2$/TFA (1:1, v:v) was stirred at ambient temperature for 30 min, concentrated in vacuo, then added $Et_2O$ to precipitate a white solid. The solid was filtered, washed with $Et_2O$, then dissolved and washed into a tarred flask with acetone. Concentration in vacuo provided a white solid, which may be used as is in the next step.

To a cooled (0°) flask containing 0.104 g (0.21 mmol) of N-Fmoc-3,5-dinitro-L-tyrosine and 0.109 g (0.21 mmol) of PyBOP is added 0.3 mL of DMF (anhydr.) and the solution stirred at 0° for ~10 min. The solution is transferred via syringe with dropwise addition to a cooled (0°) solution of the crude deprotected amine (0.17 mmol) in 0.1 mL of DMF. To this is added 0.11 mL (0.63 mmol) of N,N-diisopropylethylamine and the solution stirred to ambient temperature overnight (15 h). The resultant solution is concentrated, generally to a thick residue, via short-path distillation (40°/in vacuo), then diluted with EtOAc and washed successively with 5% aqueous citric acid, saturated aqueous $NaHCO_3$, $H_2O$, and brine. Workup followed by chromatography in 50:1 ($CH_2Cl_2$/MeOH) yields the coupled product VII.

The diastereomeric mixture 1(f, g) was purified to individual components upon coupling to H-Ile-OMe.HCl, using conditions outlined in Scheme III, to provide compounds VIII and IX. Compound VIII is converted to product 1(i) as previously described.

Synthesis of Compound 1(l)

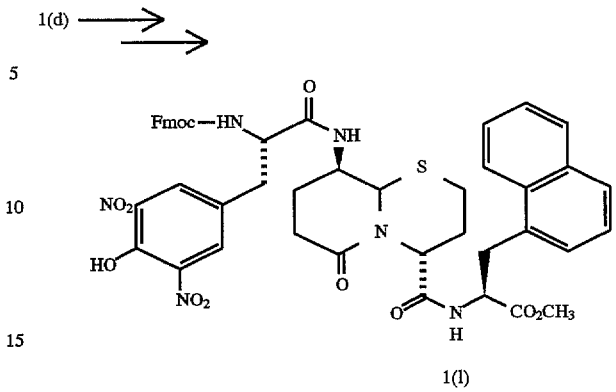

1(l)

Compound 1(l) may be synthesized as previously described utilizing H-α-Nal-OMe.HCl and N-Fmoc-3,5-dinitro-L-tyrosine. The derivatized amino acid H-α-Nal-OMe.HCl was prepared analogously to H-D-Cys-OMe.HCl starting with Boc-α-Nal-OH. Under the conditions of the reaction the Boc protecting group was removed.

Synthesis of Compound 1(m)

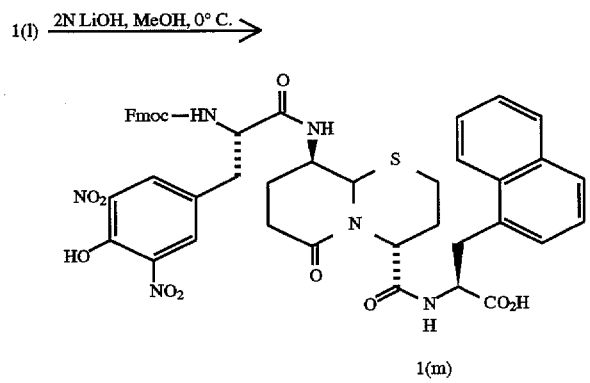

1(m)

Compound 1(l) is converted to the carboxylic acid 1(m) using LiOH, as depicted in Scheme III.

Synthesis of Compound 1(n)

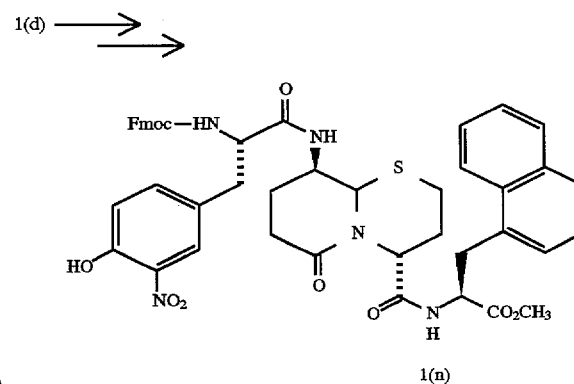

1(n)

Compound 1(n) may be synthesized as previously described utilizing H-α-Nal-OMe.HCl and N-Fmoc-3-nitro-L-tyrosine. The derivatized amino acid H-α-Nal-OMe.HCl was prepared analogously to H-D-Cys-OMe.HCl starting with boc-Nal-OH. Under the conditions of the reaction the Boc protecting group was removed.

Synthesis of Compound 1(o)

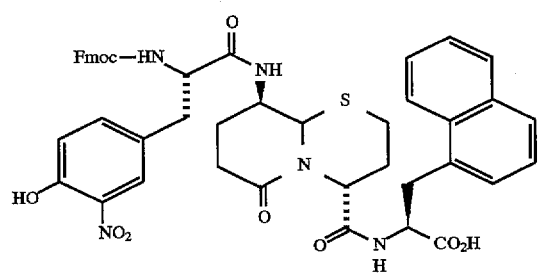

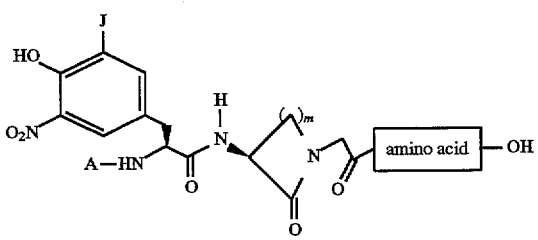

is depicted below:

Cbz: BnOCO—

Compound 1(n) is converted to the carboxylic acid 1(m) using LiOH, as depicted in Scheme III.

Synthesis of Additional Compounds

Illustrating compounds of the following structure (or esters, amides, carbamates or salts thereof):

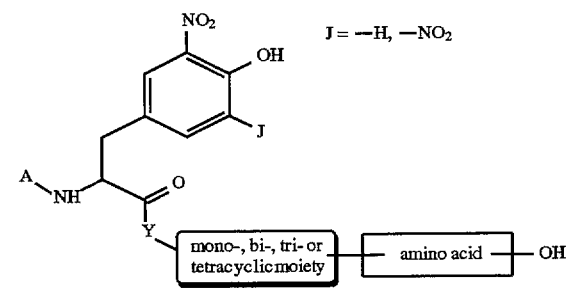

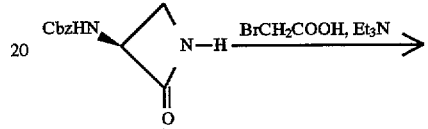

(i)

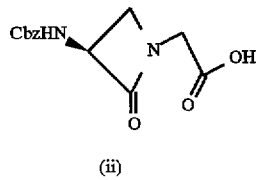

(ii)

Ile.OMe, iPr$_2$NEt, CH$_2$Cl$_2$
(ii) $\xrightarrow{\text{PyBOP, 0° C.}}$ are the compounds tabulated in the following table, each of which can be prepared by the methods described herein.

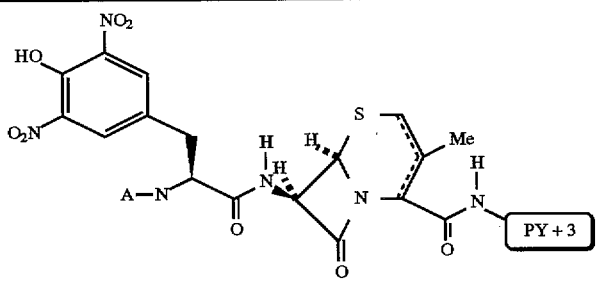

| A | Δ | PY + 3 |
|---|---|--------|
| Fmoc | 2 | Ile.OMe |
| Fmoc | 3 | Ile.OMe |
| Boc | 2 | Ile.NH$_2$ |
| Boc | 3 | Ile.NH$_2$ |
| Fmoc | 2 | Ile.NH$_2$ |
| Fmoc | 3 | Ile.NH$_2$ |

(where Δ indicates the location of the double bond in the 6-membered heterocycle).

A general synthetic route to related monocyclic compounds of the formula:

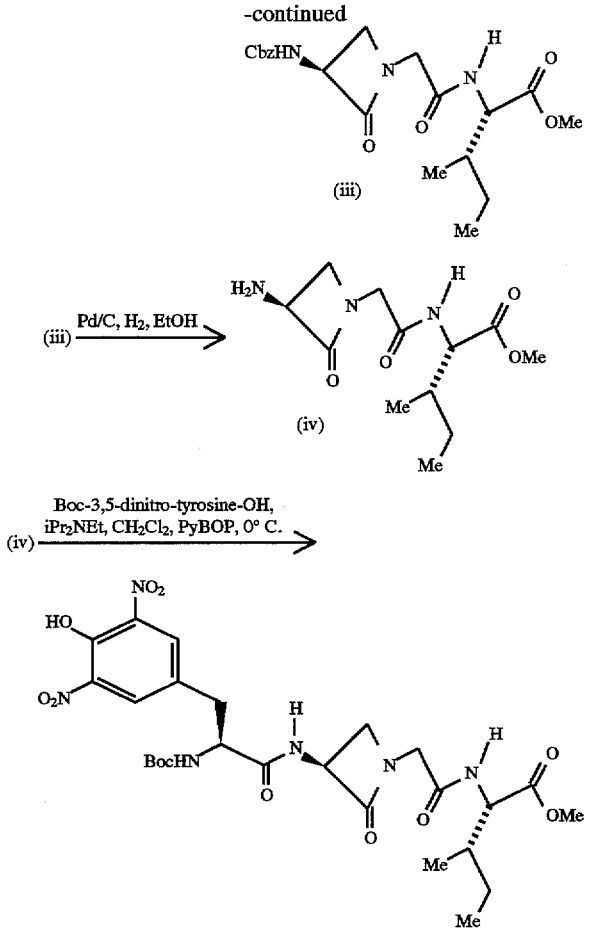

IV. Binding Assays

Competitive Binding Assays:

Binding was measured by competition using surface plasmon resonance (Malmqvist, M. (1993) *Current Opinions in Immunology* 5, 282–286) as implemented in the BIAcore Biosensor (Pharmacia Biosensor, Piscataway, N.J.). SH2proteins, e.g. pp60$^{src}$, pp70$^{ZAP}$, or pp72$^{syk}$, were pre-incubated with various concentrations of test compound and the ability of the test compound to competitively inhibit binding to a phophopeptide ligand measured. Results were compared to binding measured in the absence of competitor and expressed as percent inhibition. IC50values reflect the concentration of inhibitor required to reduce binding by 50%. Specifics of individual assays are described below. All asssays were run in HEPES Buffered Saline (HBS) composed of 10 mM HEPES (pH 7.4)/150 mM NaCl/3.4 mM EDTA/0.05% Surfactant P20at 25° C. and a flow rate of 5 uL min$^{-1}$.

Specifics of Tandem Syk Assay:

A pp72$^{syk}$ peptide ligand corresponding to the γ-chain ITAM of human Fc$_\epsilon$RI [DGVY(PO$_4$)TGLSTRNQETY(PO$_4$)ETLK] [SEQ ID NO:18] was synthesized as part of a larger peptide [Ac-CGGDGVY(PO$_4$)TGLSTRNQETY-(PO$_4$)ETLK-NH2] [SEQ ID NO:19] and used to generate a Syk-sensitive biosensor surface. Specifically, a Biosensor Chip CM5was activated with 200 mM ethyl-3-(3-dimethylaminopropyl)-carbodiimide hydrochloride (EDC)/50 mM N-hydroxysuccinimide (NHS) to generate a surface reactive to primary amines; treated with ethylenediamine to generate a surface rich in primary amines; activated with m-maleimidobenzoyl-N-hydroxysuccinimide ester (sulfo-MBS; 50 mM in 25 mM NaHCO$_3$) to generate a surface reactive to free thiols; and the ITAM peptide immobilized through the N-terminal cysteine. Unreacted sites were blocked with β-mercaptoethanol and the chip cleaned of noncovalently bound peptide using 6M guanidine hydrochloride. Assays were run in HBS using 20 nM pp72$^{syk}$ (1–265)±test inhibitor.

Specifics of C-Syk Assay:

A pp72$^{syk}$ peptide ligand corresponding to a hemiphosphorylated γ-chain ITAM of human Fc$_\epsilon$RI [DGVY(PO$_4$)TGLSTRNQETYETLK] was synthesized as part of a larger peptide [Ac-CGGDGVY(PO$_4$)TGLSTRNQETYETLK-NH$_2$] and used to generate a C-Syk-sensitive biosensor surface as described above for tandem syk. Assays were run in HBS using 270 nM pp72$^{syk}$(163–265)±test inhibitor.

Specifics of Tandem ZAP Assay:

A pp70$^{ZAP}$ peptide ligand corresponding to the ζ-chain ITAM-1 of the human T-cell receptor [NQLY(PO$_4$)NELNIGRREEY(PO$_4$)DVLD] [SEQ ID NO:20] was synthesized as a part of a larger peptide [Ac-KGGNQLY(PO$_4$)NELNIGRREEY-(PO$_4$)DVLD-NH$_2$] [SEQ ID NO:21] and used to generate a ZAP-sensitive biosensor surface. Specifically, a Biosensor Chip CM5was activated with 200 mM EDC/50 mM NHS to generate a surface reactive to primary amines and the ITAM peptide immobilized through the N-terminal lysine. Unreacted sites were blocked with ethanolamine (1M in water) and the chip cleaned of noncovalently bound peptide using 6M guanidine hydrochloride. Assays were run in HBS using 10 nM pp70$^{ZAP}$(1–259) ±test inhibitor. (The designation "b22" indicates use of a corresponding γ-chain ITAM for the ζ-chain ITAM.)

Specifics of Src Assay:

A p60$^{src}$ peptide ligand corresponding to the hamster Middle-T antigen [QY(PO4)EEIPI] [SEQ ID NO:22] was synthesized as a part of a larger peptide [Ac-KGGQY(PO4)EEIPI-NH$_2$] [SEQ ID NO:23] and used to generate a src-sensitive biosensor surface as described above for tandem ZAP. Assays were run in HBS using 270 nM pp60$^{src}$ (144–251)±test inhibitor.

Representative binding data (μM) for various compounds and a number of different SH2domains is shown in the tables below:

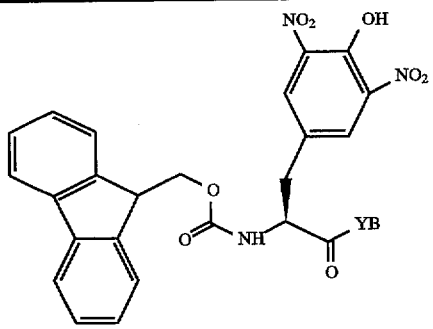
| YB = | C—Syk IC-50 | N,C—Syk 1%/Min | N,C—Syk IC-50 | N,C—Zap IC-50 | Src IC-50 |
|---|---|---|---|---|---|
| —ETL—NH₂ | 30 | 38,49 | 80,81 | 350 20(b22) | >1000 |
| —TGL—NH₂ | | | 35% @ 23 | | |
| —NEL—NH₂ | | | 15% @ 50 | 10% @ 50 | 5% @ 50 |
| —DVL—NH₂ | | | 24,30 | >100 | 25% @ 100 |
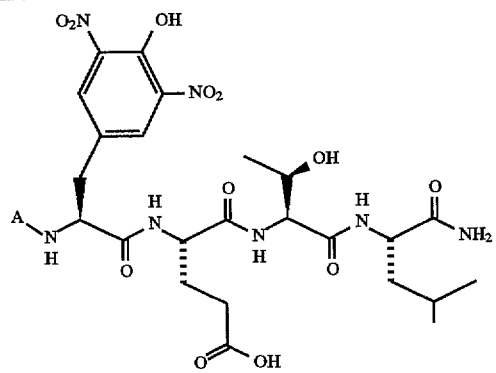
| A = | C—Syk IC-50 | N,C—Syk 1%/Min | N,C—Syk IC-50 | N,C—Zap IC-50 | Src IC-50 |
|---|---|---|---|---|---|
| 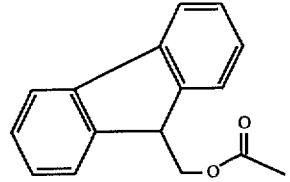 | 30 | 38 | 80 | 350 20(b22) | >1000 |
| 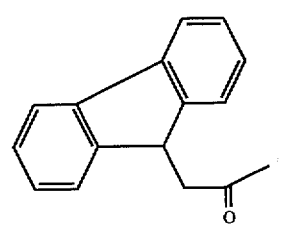 | 26 | 13 | 50 | >100 | 710 |
| 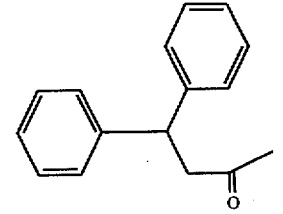 | 15 | 13 | 100 | ni @ 1000 | >1000 |

-continued

| Structure | | | | | |
|---|---|---|---|---|---|
| 1-naphthyl-CH2-C(O)-CH3 | 24 | 14 | 100 | >100 | >1000 |
| 2-naphthyl-CH2-C(O)-CH3 | 20 | 17 | 30% @ 50 | >100 | 500 |
| Ph-CH2-C(O)-CH2CH2CH3 | 43 | 48 | 240 | >100 | >1000 |
| Ph-CH2CH2-C(O)-CH3 | 11 | 12 | 460 | >100 | 410 |
| Ph-CH2-C(O)-CH3 | 70 | 23 | >1000 | >1000 | >1000 |
| 2-naphthyl-C(O)-CH3 | 35 | 67 | 380 | ni @ 100 | >1000 |
| Ph-CH(CH3)-CH2-C(O)-CH3 | 25 | 14 | 450 | >100(b22) | 800 |
| AcNH-CH(CH2Ph)-C(O)-CH3 | 200 | >500 | | >100 | >1000 |
| AcNH-CH(CH2Ph)-C(O)-CH3 (other stereo) | 50 | 180 | | >100 | 500 |
| AcNH-CH(CH2-2-naphthyl)-C(O)-CH3 | >500 | >500 | | >100 | >500 |

-continued

| | 200 | 800 | >100 | >500 |

What is claimed is:

1. A compound of the formula:

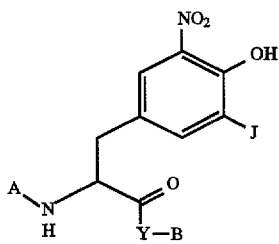

wherein

A is H, R$^1$, —CO—R$^1$ or —CO—OR$^1$ where R$^1$ is alkyl, heteroalkyl, aryl or heteroaryl;

Y is —CH$_2$—, —O—, or —NH—;

J is H or —NO$_2$; and

B is alkyl or aryl, which may be linear, branched or cyclic, and is optionally substituted, with the provisos that where J is —NO$_2$ and A is tBOC or triflouroacetyl, YB is not —OEt; where J is —NO$_2$ and A is acetyl, YB is not —OEt, —OMe, or L-Phe; and where J is —NO$_2$ and A is H, L-phenylalanyl- or N-cbz-L-phenylalanyl-, YB is not —OMe, and where J is H and A is —COOR$^1$ and R$^1$ is a branched alkyl or arylalkyl moiety, YB is a moiety other than an amino acid ester or an ester of a terapeptide, and where J is H and A is —COR$^1$ and R$^1$ is a straight chain aliphatic moiety, YB is a moiety other than ethoxy.

2. A compound of claim 1 in which R$^1$ contains at least one aryl substituent.

3. A compound of claim 1 in which YB comprises an amino acid, dipeptide, tripeptide or tetrapeptide, or an ester, amide, carbamate or salt thereof.

4. A compound of claim 1 in which YB comprises a substituted or unsubstituted monocyclic, bicyclic or tricyclic moiety.

5. A compound of the formula:

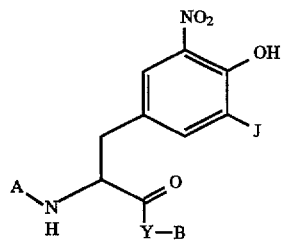

wherein

A is —CO—OR$^1$ where R$^1$ is or contains an aryl or heteroaryl moiety;

Y is —CH$_2$—, —O—, or —NH—;

J is H or —NO$_2$; and

B is H, or is alkyl or aryl, which may be linear, branched or cyclic, and is optionally substituted, with the provisos that where R1 is t-butyl, YB is not -OEthyl; where J is H and A is Z, YB is a moiety other than an amino acid ester or an ester of a tetrapeptide.

6. N-Fmoc-3,5-dinitro-L-tyrosine or an ester, amide, acid halide or salt thereof.

7. A compound of claim 1 which is capable of binding to an SH2domain with an affinity of greater than 50 µM.

8. A composition comprising a compound of claim 7 and a pharmaceutically acceptable carrier.

* * * * *